United States Patent
Andrade et al.

(10) Patent No.: US 10,406,302 B2
(45) Date of Patent: Sep. 10, 2019

(54) INHALATOR

(75) Inventors: Laura Andrade, Guadalajara (ES);
Jose Ramon Ruiz, Guadalajara (ES);
Celestino Ronchi, Guadalajara (ES);
Alessandro Castellucci, Guadalajara (ES)

(73) Assignee: LABORATORIOS LICONSA, S.A., Barcelona (ES)

( * ) Notice: Subject to any disclaimer, the term of this patent is extended or adjusted under 35 U.S.C. 154(b) by 943 days.

(21) Appl. No.: 13/992,200

(22) PCT Filed: Dec. 5, 2011

(86) PCT No.: PCT/EP2011/071775
§ 371 (c)(1),
(2), (4) Date: Jun. 6, 2013

(87) PCT Pub. No.: WO2012/076479
PCT Pub. Date: Jun. 14, 2012

(65) Prior Publication Data
US 2013/0255679 A1  Oct. 3, 2013

(30) Foreign Application Priority Data
Dec. 6, 2010  (GB) .................................. 1020638.1

(51) Int. Cl.
*A61M 15/00*  (2006.01)
*A61M 15/08*  (2006.01)

(52) U.S. Cl.
CPC ...... *A61M 15/0028* (2013.01); *A61M 15/003* (2014.02); *A61M 15/0026* (2014.02);
(Continued)

(58) Field of Classification Search
CPC .............. A61M 15/00; A61M 15/0063; A61M 15/0041; A61M 15/0026; A61M 15/08;
(Continued)

(56) References Cited

U.S. PATENT DOCUMENTS 5,070,870 A    12/1991   Pearce
5,638,957 A *   6/1997   Brasier ................. A61F 13/551
                                                              206/581
(Continued)

FOREIGN PATENT DOCUMENTS

EP       2082759 A1    7/2009
GB      2407042 A     4/2005
(Continued)

OTHER PUBLICATIONS

International Search Report and Written Opinion of the International Searching Authority, International Application No. PCT/EP2011/071775, International Filing Date Dec. 5, 2011, ISR dated Feb. 15, 2012, 12 pages, European Patent Office, Rijswijk Netherlands.

*Primary Examiner* — Colin W Stuart
*Assistant Examiner* — Douglas Y Sul
(74) *Attorney, Agent, or Firm* — Peter B. Scull; HDC IP Law LLP

(57) ABSTRACT

An inhalator for the inhalation of powdered drug preparations from capsules which contain the powdered preparations. The inhalator has a mouthpiece or nosepiece and an assembly including: a capsule holder including a capsule chamber, the capsule chamber having an air inlet opening and an air outlet opening; a capsule opening device for opening a capsule; a finger-operable actuator. The inhalator further includes a rigid outer shell including a lower shell part hinged to an upper shell part so that the shell is openable and closable, the shell serving to cover and protect the assembly and the mouthpiece or nosepiece. The assembly and the mouthpiece or nosepiece are removable as a hinged unit from the open shell as a hinged unit without dismantling either unit, or the shell is arranged so that the contours of the rim of each shell part match the contours of the rim of the other around each shell part when the shell is in the closed (Continued)

condition, or the assembly is retained in the lower shell part and is not moveable in normal use with respect to the lower shell part.

10 Claims, 18 Drawing Sheets

(52) U.S. Cl.
CPC .... *A61M 15/0035* (2014.02); *A61M 15/0041* (2014.02); *A61M 15/0063* (2014.02); *A61M 15/08* (2013.01); *A61M 2202/064* (2013.01)

(58) Field of Classification Search
CPC .......... A61M 2202/064; A61M 15/003; A61M 15/0035
See application file for complete search history.

(56) References Cited

U.S. PATENT DOCUMENTS

| | | | |
|---|---|---|---|
| 5,685,294 A | 11/1997 | Gupte et al. | |
| 5,947,118 A | 9/1999 | Hochrainer et al. | |
| 7,080,754 B2 * | 7/2006 | Lown | B65D 43/164 220/324 |
| 7,235,740 B2 * | 6/2007 | Dinh | H02G 3/14 174/66 |
| 2003/0235538 A1 * | 12/2003 | Zierenberg | A61K 9/0075 424/46 |
| 2005/0258191 A1 * | 11/2005 | Davies | A61M 15/08 222/162 |
| 2007/0012316 A1 * | 1/2007 | Truza | A61M 15/00 128/200.23 |
| 2007/0295332 A1 * | 12/2007 | Ziegler | A61M 15/0028 128/203.15 |
| 2008/0175887 A1 * | 7/2008 | Wang | A61K 31/337 424/434 |
| 2008/0269689 A1 * | 10/2008 | Edwards | A61M 5/2053 604/189 |
| 2009/0277446 A1 * | 11/2009 | Walz | A61M 15/0028 128/203.15 |
| 2010/0275917 A1 * | 11/2010 | Kuhn | A61M 15/0028 128/203.15 |
| 2011/0120465 A1 * | 5/2011 | Haerder | A61M 15/0028 128/203.15 |
| 2011/0232637 A1 * | 9/2011 | Kaemper | A61M 15/0028 128/203.12 |
| 2013/0047985 A1 * | 2/2013 | Harris | A61M 15/0028 128/203.15 |
| 2014/0318538 A1 * | 10/2014 | Bilgic | A61M 15/0028 128/203.15 |

FOREIGN PATENT DOCUMENTS

| | | |
|---|---|---|
| RU | 2369411 C2 | 10/2009 |
| WO | WO9102558 A1 | 3/1991 |
| WO | WO94/28958 A1 | 12/1994 |
| WO | WO2009092593 A1 | 7/2009 |
| WO | WO2009/151408 A2 | 12/2009 |

* cited by examiner

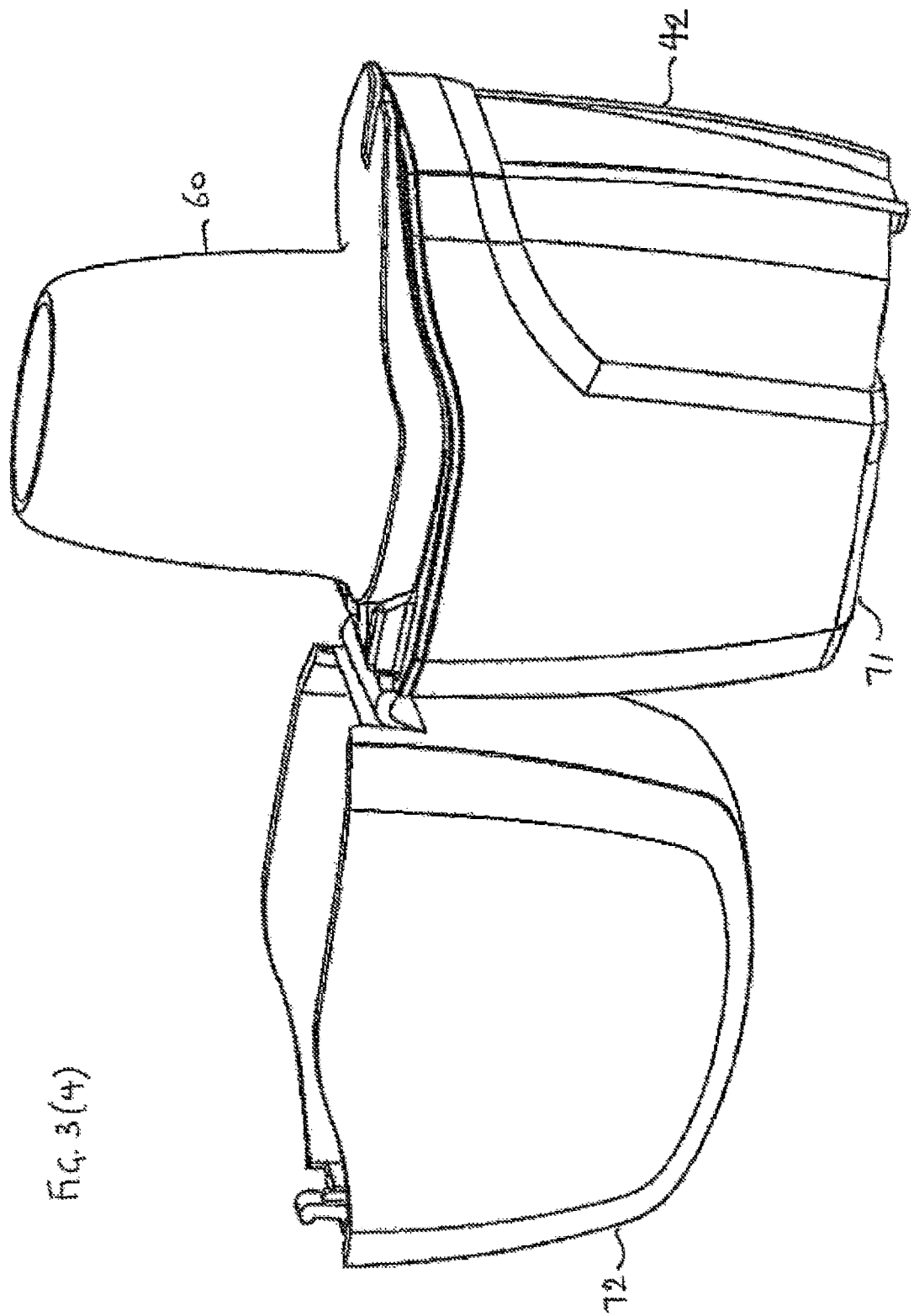

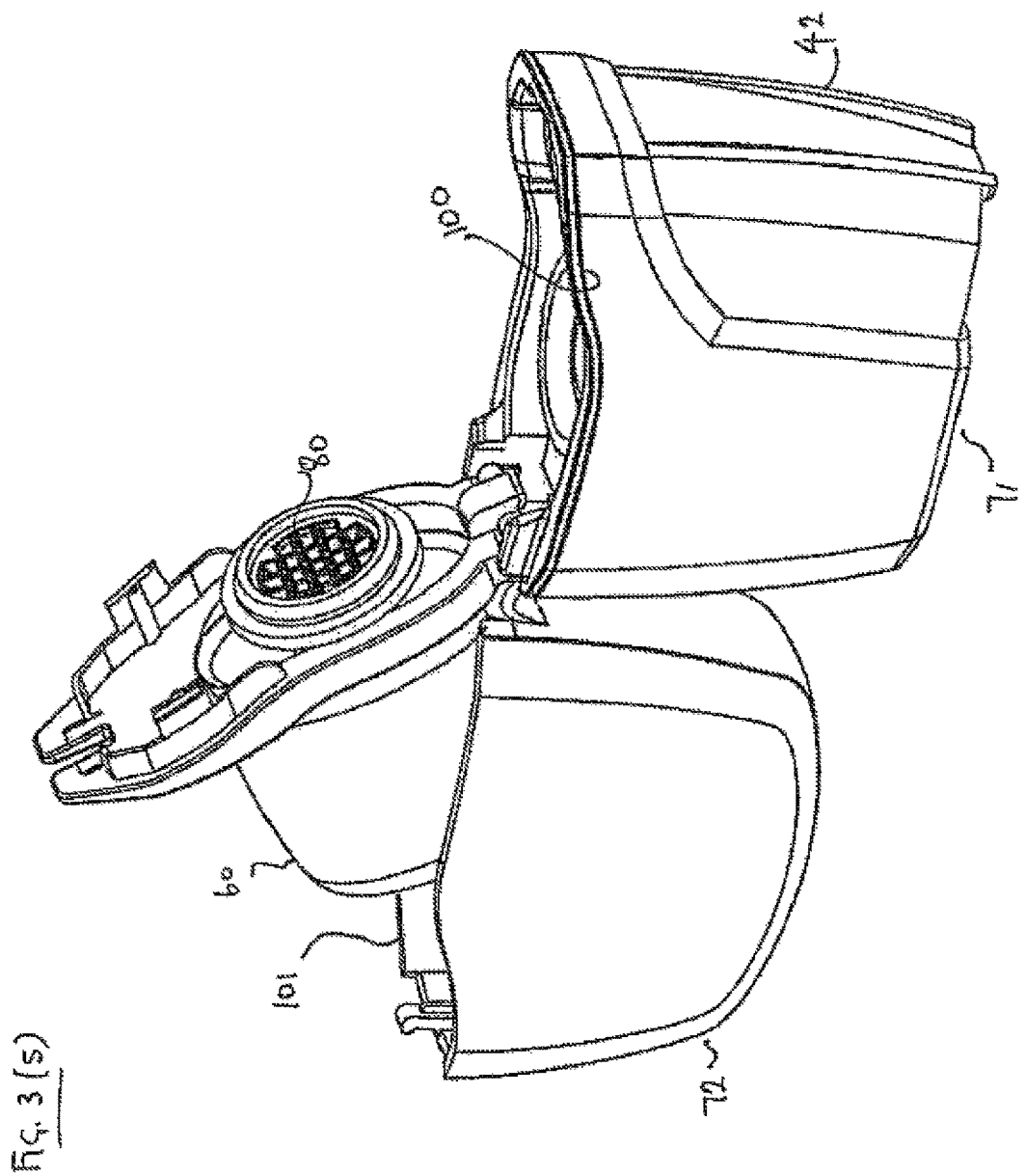

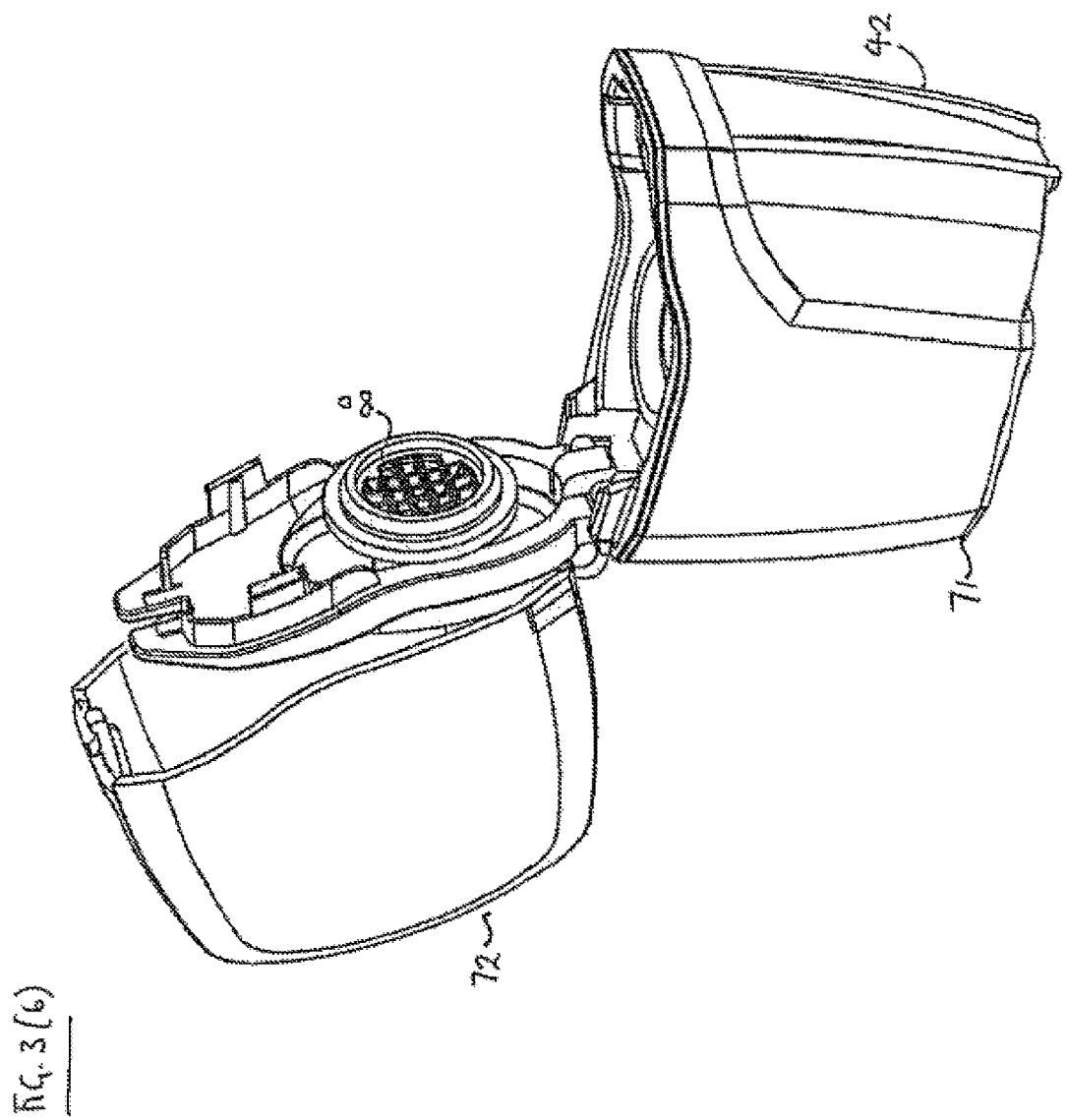

Fig. 8
(1)
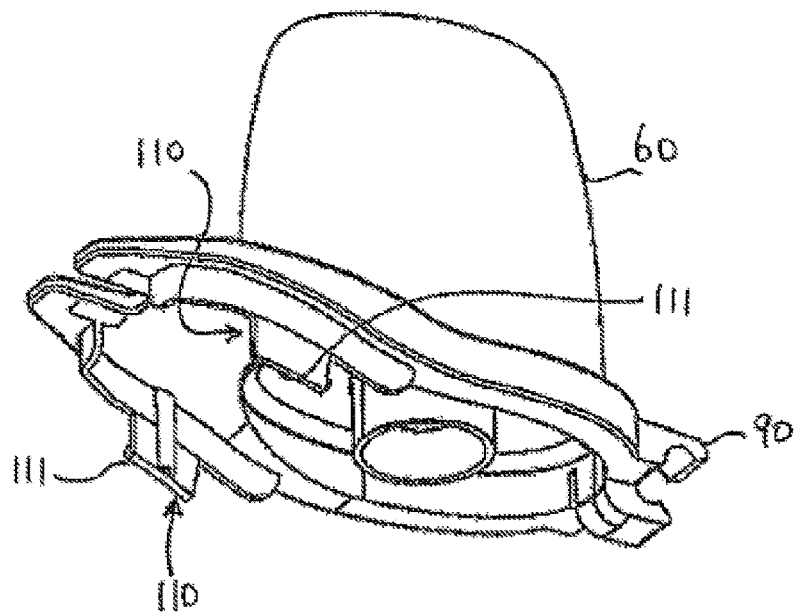
(2)
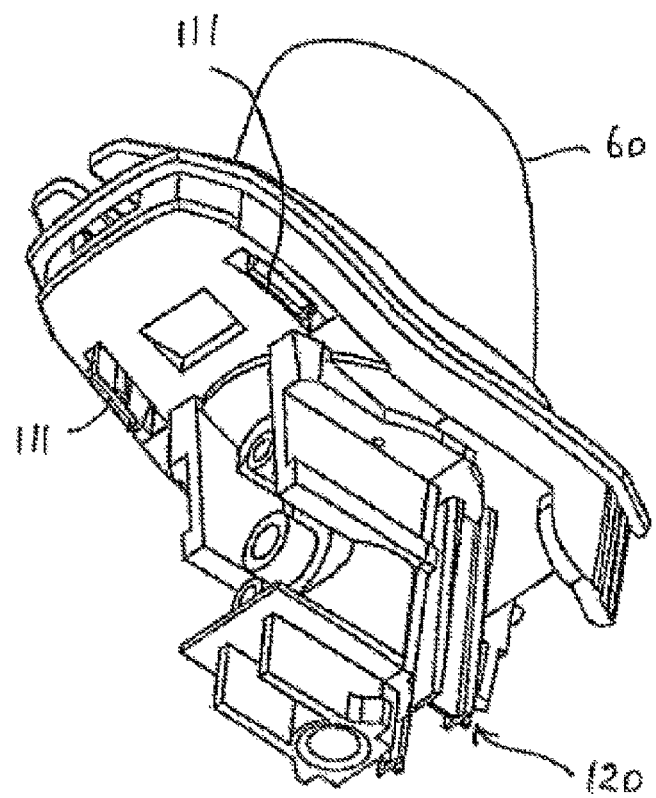

INHALATOR

TECHNICAL FIELD

The present disclosure relates to inhalators for the inhalation of solid medicaments in powder form, particularly medicament powders provided in capsules for use with the inhalator.

BACKGROUND

WO-A-94/28958, the disclosure of which is incorporated herein by reference, describes a powder inhaler (inhalator) for the inhalation of powdered drug preparations from capsules which contain the powdered preparations. The inhalator includes an assembly of a capsule holder including a capsule chamber for receiving a capsule containing the powdered preparation, the capsule chamber having an air inlet opening and an air outlet opening, a capsule opening device associated with the capsule chamber for opening a capsule within the chamber, and a finger-operable actuator for the capsule opening device. In the known inhalator, the capsule opening device includes pins which can be reciprocally moved into and out of the chamber to pierce the capsule. The inhalator further includes a mouthpiece which is arranged downstream from the air outlet opening. After the capsule has been received in the chamber and opened using the capsule opening device, the user sucks air through the capsule chamber, entraining the powder from the capsule in the airflow out of the chamber, through the mouthpiece and thence into the user's lungs. The spent capsule is discarded after use.

FIG. 1 of the accompanying drawings reproduces FIG. 6 of the known inhalator, and illustrates an exploded view of such an inhalator in which an assembly of the capsule holder, the capsule opening device and the actuator for the capsule opening device (1, 8, 9, 10) is directly hinged to the mouthpiece (12, 13). The mouthpiece is thereby pivotable towards and away from the air outlet of the capsule chamber for charging and cleaning out the chamber.

The hinge element is a pin hinge system which serves as a common hinge pin (direct mutual hinging) for the assembly and the mouthpiece and serves also to hinge together the two halves of a hinged rigid outer shell including a lower shell part (6) and an upper shell part (15). The lower shell part serves to house and protect the assembly of the capsule holder, the capsule opening device and the finger-operable actuator for the capsule opening device, and the upper shell part serves to cover the mouthpiece when the inhalator is not in use.

The assembly of the capsule chamber, the capsule opening device and the finger-operable actuator for the capsule opening device can be pivoted away from the lower shell part (6), and for this purpose the rim of the lower shell part is cut away at A so that a finger button (10) of the finger-operable actuator for the capsule opening device protrudes through the lower shell part yet can still be pivoted up and away from the shell part.

This construction is complex and contains many mechanical parts. Dismantling or partially dismantling the known inhalators, for example for cleaning, is generally difficult or impossible for the average user. Cleaning around the hinge is especially difficult. Moreover, breakage of the hinge makes the whole device unusable.

It would be desirable to simplify the construction of such inhalators, and in particular to provide an inhalator that can more easily be cleaned.

Furthermore, it is inconvenient for a user to personalize their inhalator as the whole inhalator must be discarded after its useful life. It would be desirable to have an inhalator where an external part could be reused.

An inhalator having a reusable part would also enable treatment regimen recorders, prompters, calculators or other assisting devices, for example electronic devices, to be associated with the inhalator.

The present disclosure as described below provides an alternative and/or improved inhalator.

SUMMARY

In a first aspect there is provided an inhalator for the inhalation of powdered drug preparations from capsules which contain the powdered preparations, the inhalator including:
(a) an assembly including:
a capsule holder including a capsule chamber for receiving a capsule containing the powdered preparation, the capsule chamber having an air inlet opening and an air outlet opening;
a capsule opening device associated with the capsule chamber for opening a capsule within the chamber;
a finger-operable actuator for the capsule opening device; and
(b) a mouthpiece or nosepiece;
whereby the user can suck air through the air inlet opening, into the capsule chamber to entrain powder from the opened capsule, and then out of the chamber through the air outlet opening and the mouthpiece or nosepiece, and thence into the user's lungs;
wherein the assembly (a) and the mouthpiece or nosepiece (b) are mutually hinged so that the mouthpiece or nosepiece can pivot between an open condition in which the mouthpiece or nosepiece is spaced apart from the air outlet opening of the capsule chamber for loading the capsule into the capsule chamber and a closed condition in which the mouthpiece or nosepiece is disposed in airflow communication with the air outlet opening of the capsule chamber for use;
and wherein the inhalator further includes:
(c) a rigid outer shell including a lower shell part hinged to an upper shell part so that the shell is openable and closable;
wherein
the assembly (a) and the mouthpiece or nosepiece (b) define a first hinged unit and the outer shell (c) defines a second hinged unit, the first hinged unit being disposed within the second hinged unit for use such that the first hinged unit can be removed as such from the second hinged unit as such.

The arrangement is particularly characterized in that the hinges of the two units are separate from one another. In particular, the hinge of the first unit is separate and operates independently of the hinge of the second unit. The first unit can be removed from the second unit without affecting the construction or operation of either hinge.

It is preferred that, when the first hinged unit is received in the second hinged unit, the assembly (a) portion of the first hinged unit is received substantially completely within the lower shell part of the outer shell. In this way the upper shell part can serve as a cover for the mouthpiece or nosepiece (b) when the inhalator is not in use.

It is also preferred that the inhalator has a single capsule chamber, preferably generally centrally disposed on a central longitudinal axis of the inhalator. This single chamber must be emptied and reloaded with a capsule between each use.

In particular, it is preferred that the inhalator does not include a revolver-type magazine of the type described in WO-A-91/02558, wherein two or more—for example 6—chambers can be loaded with up to that number of capsules in advance and each one aligned with the capsule opening device for each successive inhalation procedure up to the maximum of the number of capsules in the inhalator.

The capsule is preferably a conventional pharmaceutical capsule containing powdered medicament. Capsules of any suitable physiologically acceptable capsule material may be used, for example capsules derived from animal proteins (e.g. gelatine) or plant polysaccharides (e.g. gums, starch and cellulose). Suitable capsules include those formed from gelatin, hydroxypropylmethyl cellulose or hydroxypropyl cellulose. The expression "capsule" used herein shall be understood broadly, to refer to all closed containers holding the powdered medicament or drug preparation to be inhaled, and openable for said inhalation using the present inhalator.

The parts of the rigid outer shell of the inhalator are hollow and each has a circumferential rim defining an open mouth of the part. It is preferred that the outer shell of the inhalator is arranged so that the contours of the rim of one shell part match the contours of the rim of the other completely or at least substantially circumferentially around the rims when the shell is in the closed condition. The expression "match the contours" used herein in relation to the rims of the outer shell parts means particularly that the rims in the closed condition of the shell are either touching or are within about 10 mm, for example within about 5 mm, of each other over all of the circumferential portion of the rims not occupied by the hinge between the shell parts. In one example, the rim of each shell part matches the rim of the other shell completely and one is not cut away, e.g. as in the known inhalator as discussed above.

In a preferred implementation, therefore, the lower shell part of the outer shell is tapered inwardly in the downward direction away from a top opening defined by its rim, the assembly (a) of the first hinged unit correspondingly tapers inwardly in the downward direction so that it can be received in the lower shell part, and the finger-operable actuator for the capsule opening device protrudes through an opening in the lower shell part below the rim of the lower shell part, whereby the rim of the lower shell part is complete and the first hinged unit can be removed from the lower shell part by passing up and through the top opening defined by the rim of the lower shell part.

This arrangement has the technical advantage that the two shell parts are more rigid and robust than the arrangement of the known inhalators, in which the rim of the lower shell part was cut away.

In a second aspect there is provided an inhalator for the inhalation of powdered drug preparations from capsules which contain the powdered preparations, the inhalator including:
(a) an assembly including:
a capsule holder including a capsule chamber for receiving a capsule containing the powdered preparation, the capsule chamber having an air inlet opening and an air outlet opening;
a capsule opening device associated with the capsule chamber for opening a capsule within the chamber;
a finger-operable actuator for the capsule opening device; and
(b) a mouthpiece or nosepiece;
whereby the user can suck air through the air inlet opening, into the capsule chamber to entrain powder from the opened capsule, and then out of the chamber through the air outlet opening and the mouthpiece or nosepiece, and thence into the user's lungs;
wherein the assembly (a) and the mouthpiece or nosepiece (b) are mutually hinged so that the mouthpiece or nosepiece can pivot between an open condition in which the mouthpiece or nosepiece is spaced apart from the air outlet opening of the capsule chamber for loading the capsule into the capsule chamber and a closed condition in which the mouthpiece or nosepiece is disposed in airflow communication with the air outlet opening of the capsule chamber for use;
and wherein the inhalator further includes:
(c) a rigid outer shell including a lower shell part hinged to an upper shell part so that the shell is openable and closable;
wherein
the assembly (a) and the mouthpiece or nosepiece (b) are disposed within the outer shell, each of the upper and lower shell parts has a circumferential rim defining a mouth of the part and the contours of the rim of each shell part match the contours of the rim of the other substantially completely around the rims when the shell is in the closed condition.

The expression "match the contours" used in relation to the second aspect is to be understood in the same sense as defined above in relation to the first aspect.

In a preferred implementation of the second aspect, the lower shell part of the outer shell is tapered inwardly in the downward direction away from a top opening defined by its rim, the assembly (a) (e.g. the assembly (a) of the first hinged unit) correspondingly tapers inwardly in the downward direction so that it can be received in the lower shell part, and the finger-operable actuator for the capsule opening device protrudes through an opening in the lower shell part below the rim of the lower shell part, whereby the rim of the lower shell part is complete and the assembly (a) (e.g. the first hinged unit) can be removed from the lower shell part by passing up and through the top opening defined by the rim of the lower shell part.

This arrangement has the technical advantage that the two shell parts are more rigid and robust than the arrangement of the known inhalators, in which the rim of the lower shell part was cut away.

It is preferred that the assembly (a) and the mouthpiece or nosepiece (b) define a first hinged unit and the outer shell (c) defines a second hinged unit, the first hinged unit being received in the second hinged unit for use such that the first hinged unit can be removed as such from the second hinged unit as such. The arrangement is particularly characterized in that the hinges of the two units are separate from one another. In particular, the hinge of the first unit is separate and operates independently of the hinge of the second unit. The first unit can be removed from the second unit without affecting the construction or operation of either hinge.

It is preferred that, when the first hinged unit is received in the second hinged unit, the assembly (a) portion of the first hinged unit is received substantially completely within the lower shell part of the outer shell. In this way the upper shell part can serve as a cover for the mouthpiece or nosepiece (b) when the inhalator is not in use.

A further technical advantage is that means can be provided for releasably securing the upper shell part to the mouthpiece or nosepiece (b), whereby both hinged units can be manually opened simultaneously in one manual action.

This has the effect that the upper shell part and the mouthpiece or nosepiece housed within it can be hinged as a unit away from the lower shell part and the assembly (a) housed within it. This enables the capsule chamber to be exposed for loading a capsule into the chamber or for emptying or cleaning the chamber, without the user needing to touch the mouthpiece or nosepiece. The upper shell part and the mouthpiece or nosepiece can then be closed as a unit onto the lower shell part and the assembly (a) housed within it. After manually releasing the securement between the upper shell part and the mouthpiece or nosepiece, the upper shell part can then be opened on its hinge again, but this time independently of the mouthpiece or nosepiece which stays in position adjacent the assembly (a). In this open condition the inhalator, containing a capsule in the capsule chamber, is now ready for use.

It is also preferred that the inhalator of the second aspect has a single capsule chamber, preferably generally centrally disposed on a central longitudinal axis of the inhalator. This single chamber must be emptied and reloaded with a capsule between each use.

In particular, it is preferred that the inhalator of the second aspect include a revolver-type magazine of the type described in WO-A-91/02558, wherein two or more—for example 6—chambers can be loaded with up to that number of capsules in advance and each one aligned with the cutting device for each successive inhalation procedure up to the maximum of the number of capsules in the inhalator.

We have further found that the manufacture of inhalators can be significantly simplified if the assembly (a) is retained in the lower shell part and is not moveable in normal use with respect to the lower shell part. This has the advantage, for example, that the hinging between the mouthpiece or nosepiece (b) and the assembly (a) can be made indirect, particularly by providing a hinge between the lower shell part and the mouthpiece or nosepiece (b). Such a hinge serves also to hinge the mouthpiece or nosepiece (b) to the assembly (a), by virtue of the retention of the assembly (a) in the lower shell part.

In a third aspect there is thus provided an inhalator for the inhalation of powdered drug preparations from capsules which contain the powdered preparations, the inhalator including:
(a) an assembly including:
a capsule holder including a capsule chamber for receiving a capsule containing the powdered preparation, the capsule chamber having an air inlet opening and an air outlet opening;
a capsule opening device associated with the capsule chamber for opening a capsule within the chamber;
a finger-operable actuator for the capsule opening device; and
(b) a mouthpiece or nosepiece;
whereby the user can suck air through the air inlet opening, into the capsule chamber to entrain powder from the opened capsule, and then out of the chamber through the air outlet opening and the mouthpiece or nosepiece, and thence into the user's lungs;
wherein the assembly (a) and the mouthpiece or nosepiece (b) are mutually hinged so that the mouthpiece or nosepiece can pivot between an open condition in which the mouthpiece or nosepiece is spaced apart from the air outlet opening of the capsule chamber for loading the capsule into the capsule chamber and a closed condition in which the mouthpiece or nosepiece is disposed in airflow communication with the air outlet opening of the capsule chamber for use;
and wherein the inhalator further includes:
(c) a rigid outer shell including a lower shell part hinged to an upper shell part so that the shell is openable and closable;
wherein
the assembly (a) is retained in the lower shell part and is not moveable in normal use with respect to the lower shell part.

In a preferred implementation of the third aspect, the mouthpiece or nosepiece (b) is disposed within the upper part of the outer shell, each of the upper and lower shell parts has a circumferential rim defining a mouth of the part and the contours of the rim of each shell part match the contours of the rim of the other substantially completely around the rims when the shell is in the closed condition.

The expression "match the contours" used in relation to the third aspect is to be understood in the same sense as defined above in relation to the first aspect.

In a preferred implementation of the third aspect, the lower shell part of the outer shell is tapered inwardly in the downward direction away from a top opening defined by its rim, the assembly (a) correspondingly tapers inwardly in the downward direction so that it can be received in the lower shell part to be retained therein, and the finger-operable actuator for the capsule opening device protrudes through an opening in the lower shell part below the rim of the lower shell part, whereby the rim of the lower shell part is complete.

This arrangement has the technical advantage that the two shell parts are more rigid and robust than the arrangement of the known inhalators, in which the rim of the lower shell part was cut away. The retention of the assembly (a) in the lower shell part has the advantage that the hinge system and its manufacture can be simplified, hi that only the upper shell part and the mouthpiece or nosepiece need to be made pivotable with respect to the lower shell part.

Means can be provided for releasably securing the upper shell part to the mouthpiece or nosepiece (b), whereby both the upper shell part and the mouthpiece or nosepiece can be manually opened simultaneously in one manual action. This has the effect that the upper shell part and the mouthpiece or nosepiece housed within it can be hinged as a unit away from the lower shell part and the assembly (a) housed within it. This enables the capsule chamber to be exposed for loading a capsule into the chamber or for emptying or cleaning the chamber, without the user needing to touch the mouthpiece or nosepiece. The upper shell part and the mouthpiece or nosepiece can then be closed as a unit onto the lower shell part and the assembly (a) housed within it. After manually releasing the securement between the upper shell part and the mouthpiece or nosepiece, the upper shell part can then be opened on its hinge again, but this time independently of the mouthpiece or nosepiece which stays in position adjacent the assembly (a). In this open condition the inhalator, containing a capsule in the capsule chamber, is now ready for use.

It is also preferred that the inhalator of the third aspect has a single capsule chamber, preferably generally centrally disposed on a central longitudinal axis of the inhalator. This single chamber must be emptied and reloaded with a capsule between each use.

In particular, it is preferred that the inhalator of the third aspect does not include a revolver-type magazine of the type described in WO-A-91/02558, wherein two or more—for example 6—chambers can be loaded with up to that number of capsules in advance and each one aligned with the cutting device for each successive inhalation procedure up to the maximum of the number of capsules in the inhalator.

The expression "mutually hinged" used in relation to the relative movement of the assembly (a) and the mouthpiece or nosepiece (b) includes all implementations of mutual hinging, including direct and indirect, provided that the mouthpiece or nosepiece can pivot as required between the open and closed conditions relative to the assembly.

"Direct" mutual hinging is typically achieved by use of a common hinge pin or other hinge element serving the assembly (a) and the mouthpiece or nosepiece (b). "Indirect" mutual hinging is typically achieved, for example in relation to the third aspect but also in implementations of the first and second aspects, using one or two intermediary members to which respectively one or both of the assembly (a) and the mouthpiece or nosepiece (b) is/are connected, the intermediary member(s) being served by the hinge pin or other hinge element. In one preferred implementation of the third aspect, the lower shell part serves as an intermediary member for the assembly (a), whereby the assembly (a) and the mouthpiece or nosepiece (b) are indirectly mutually hinged.

The preferences and implementations described herein in relation to any aspect of the present disclosure apply to any other aspect or aspects unless specifically stated otherwise. Moreover, two or more aspects of the present disclosure may be present simultaneously in an inhalator if desired.

The following discussion applies to all aspects of the present disclosure, whether embodied simultaneously or independently in an inhalator.

The expression "mouthpiece" used in the following discussion shall be understood as referring equally to pieces for use with the mouth and the nose.

The assembly (a) and the lower shell part are preferably configured so that the former is snug-fit or push-fit into the latter for locating the assembly (a) in the lower shell part. In relation to the third aspect, it is preferred that the assembly (a) is retained in the lower shell part by cooperating formations which prevent the assembly (a) from being removed from the lower shell part by the user in normal use. Such cooperating formations may, for example, provide for snap-fit engagement to retain the assembly (a) in the lower shell part.

In one possible arrangement, not applicable to the third aspect, the mouthpiece (b) of the inhalator includes a projection extending away from the pivot line of the hinge between the mouthpiece (b) and the assembly (a) on the opposite side of the pivot line from the mouthpiece and the assembly (a) includes a stop surface arranged so that the said projection will bear against the stop surface after the mouthpiece (b) has been rotated more than a certain angle (e.g. more than about 90°, more than about 100°, more than about 110° or more than about 120°) out of a closed condition in which the mouthpiece is adjacent the air outlet opening of the capsule chamber. In this way, after the certain angle of rotation has been reached, further gentle pressure on the mouthpiece will lift the assembly (a) out of its fit in the lower shell part, which assists to remove the assembly from the shell.

It is preferred that the hinge connecting the mouthpiece to the remainder of the inhalator, for example the hinge between assembly (a) and mouthpiece (b), is a separable hinge, so that if too much pressure is exerted on the mouthpiece when pivoting it away from the assembly, for example when opening the chamber for loading or emptying the chamber, or when seeking to remove the assembly (a) and mouthpiece (b) from the shell as described in the preceding paragraph, the hinge will separate before breaking. The construction is preferably a simple snap-fit or push-fit engagement system of cooperating formations on the two parts of the hinge, so that the user in the case of separation of the parts can easily reassemble the hinge.

It is preferred that the mouthpiece (b) fits securely, but manually releasably, to the assembly (a) in a closed condition in which the mouthpiece is disposed adjacent the air outlet opening of the capsule chamber. For this purpose, cooperating formations may suitably be provided on meeting parts of the assembly (a) and the mouthpiece (b) to provide for push-fit or snap-fit engagement that is secure, but releasable with finger pressure by a normal user.

It is also preferred that the two parts of the shell fit securely, but manually releasably, to each other in the closed condition of the shell. For this purpose, cooperating formations may suitably be provided on the two parts of the shell, particularly associated with the rims of the shell parts, to provide for push-fit or snap-fit engagement that is secure, but releasable with finger pressure by a normal user.

Still further, it is preferred that the upper part of the outer shell fits securely, but manually releasably, to the mouthpiece (b) in the closed condition of the shell, so that opening of the shell by a user in preparation for use correspondingly pivots the mouthpiece (b) away from the assembly (a) to expose the capsule chamber for loading of a capsule. After loading of the capsule the mouthpiece (b) can then be released from its engagement with the upper part of the outer shell, so that the mouthpiece can be brought adjacent to the air outlet opening of the capsule chamber for use.

One or more dimension(s) of one of the upper and lower shell parts may be preferably substantially the same as the corresponding dimension(s) of the other, that is: any one or more dimension(s) of one shell part may preferably differ from the corresponding dimension(s) of the other shell part by no more than about 20%, preferably no more than 10%. All the length, width and height dimensions of one part may be substantially the same as the corresponding dimensions of the other part. The outward appearance of the two shell parts may also be substantially the same. In reckoning the relative dimensions and appearance of the two shell parts, any protruding parts of other components, for example the finger-operable actuator for the capsule opening device, shall be disregarded, namely: a comparison between the shell parts shall not be made in respect of portions of the shell parts that do not exist in both parts.

According to a further aspect of the present disclosure, the hinged units may be provided separately. In particular, the internal unit including the assembly (a) and the mouthpiece (b) may be replaceable after it has been used a number of times. This could, for example, be related to safety considerations, for example to avoid a risk of the cutting device failing or of debris clogging the chamber or other working parts. A hinged unit consisting of the upper and lower shell parts and the mouthpiece can be provided separately for use in manufacturing the inhalator according to the third aspect. The assembly (a) can then readily be introduced and retained in the lower shell part to prepare the inhalator for use. By providing, for example, that the retention of the assembly (a) in the lower shell part is releasable and by providing means for preventing unintentional release (for example, by selecting the strength of the snap-fit retention to be such that a release tool must be used to effect release), the assembly (a) can be replaced as required. The ability to replace the assembly (a) allows the life of the inhalator to be extended.

The inhalator may include treatment regimen recorders, prompters, calculators or other assisting devices, for example electronic devices. Such devices may, for example, be associated with the rigid outer shell.

In the description of the present disclosure herein, the term "including" shall be taken to mean that the inhalator may include, or may consist essentially of, or may consist only of, the stated features. In all cases, the presence of any additional features must not frustrate the explicit requirements of the definition. The expression "consist essentially of the stated features" means that other features that may be present must not substantially adversely affect the operation of the inhalator as defined.

BRIEF DESCRIPTION OF THE DRAWINGS

For further illustration of the present disclosure, one example will now be described further, without limitation and purely by way of example, with reference to the accompanying drawings, in which:

FIG. 8(1) shows a perspective view from below and the side of the mouthpiece, and FIG. 8(2) shows a perspective view from below and the side of the chamber moulding of the inner part of the inhalator with the mouthpiece snap fitted to the top of the moulding, showing the cooperating flanges for the snap fitting;

DETAILED DESCRIPTION OF THE DRAWINGS

Referring to FIGS. 2 to 10, there is shown an inhalator for the inhalation of powdered drug preparations from capsules which contain the powdered preparations.

Figure 4:
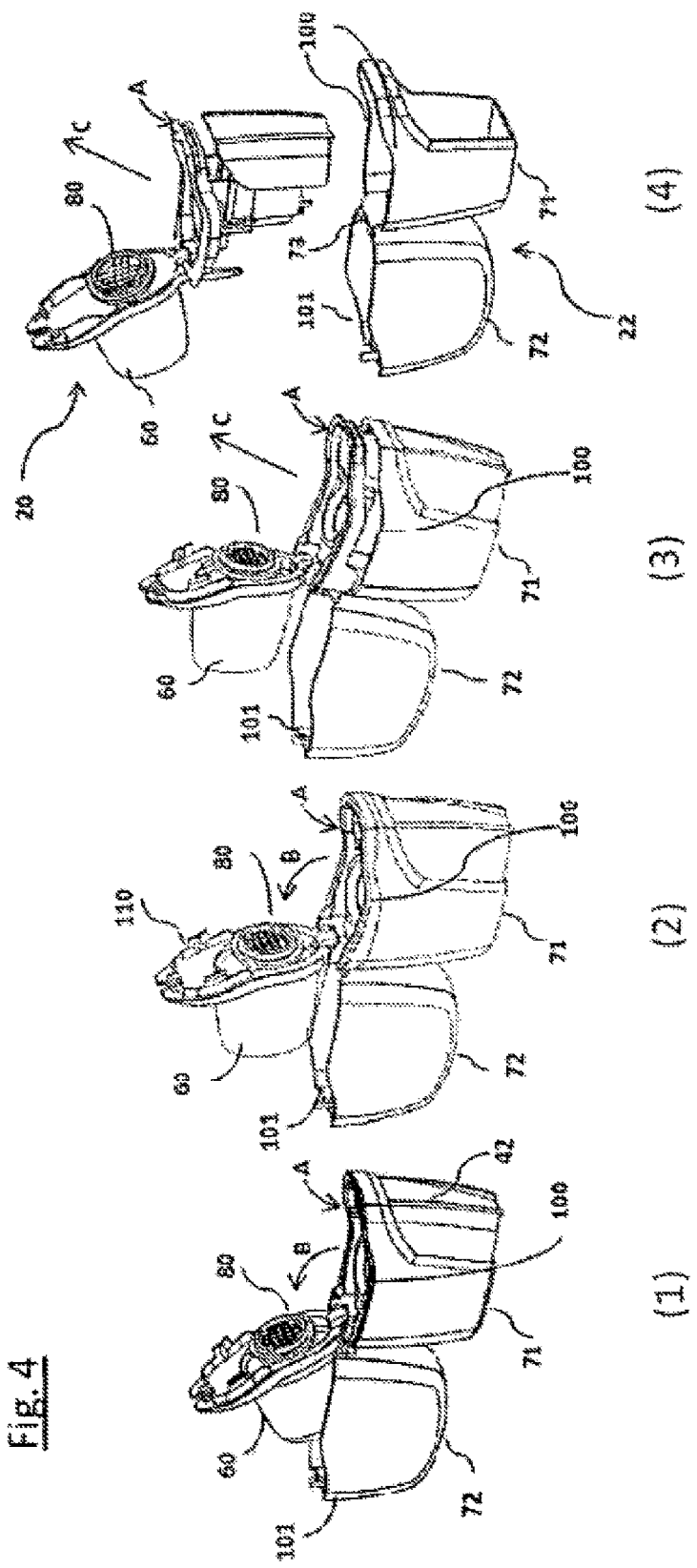
FIG. 4(1), 4(2), 4(3) and 4(4) shows the process of removing the assembly and the mouthpiece as a hinged unit from the open shell as a hinged unit without dismantling either unit.

The inhalator generally includes inner 20 and outer 22 parts (see particularly FIG. 4(4)).

Figure 10:
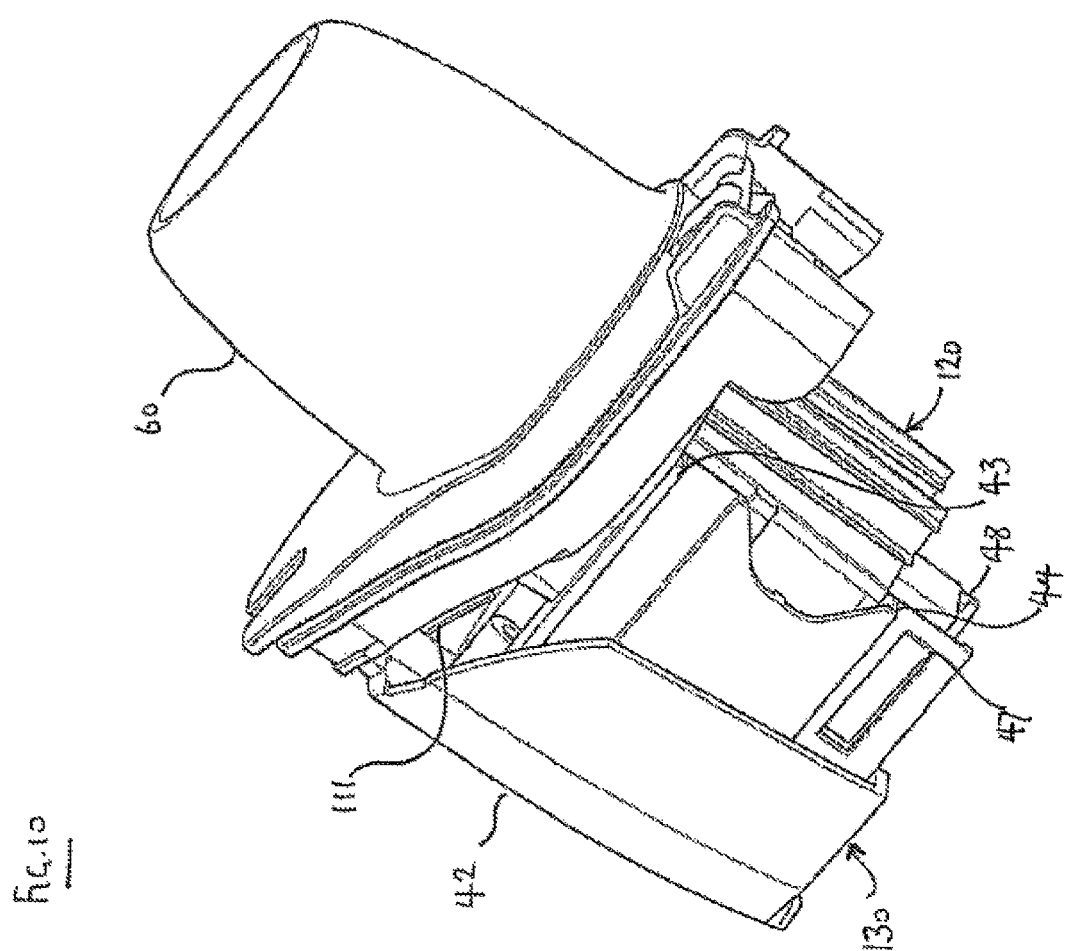
FIG. 10 shows a perspective view from below and the side of the assembly and the mouthpiece in the closed condition.

The inner part 20 is constructed in three major moulded parts, namely a mouthpiece 60, a chamber moulding 120 and an actuator moulding 130 (see FIGS. 8 and 10 in particular). In addition, pins 36, 37 are mounted to the outer moulding 130, as described in more detail below, and a spring 40 is provided between the chamber (inner) 120 and actuator (outer) 130 mouldings, as also described in more detail below.

The outer part 22 is constructed in a single moulding, as described in more detail below.

Figure 6:
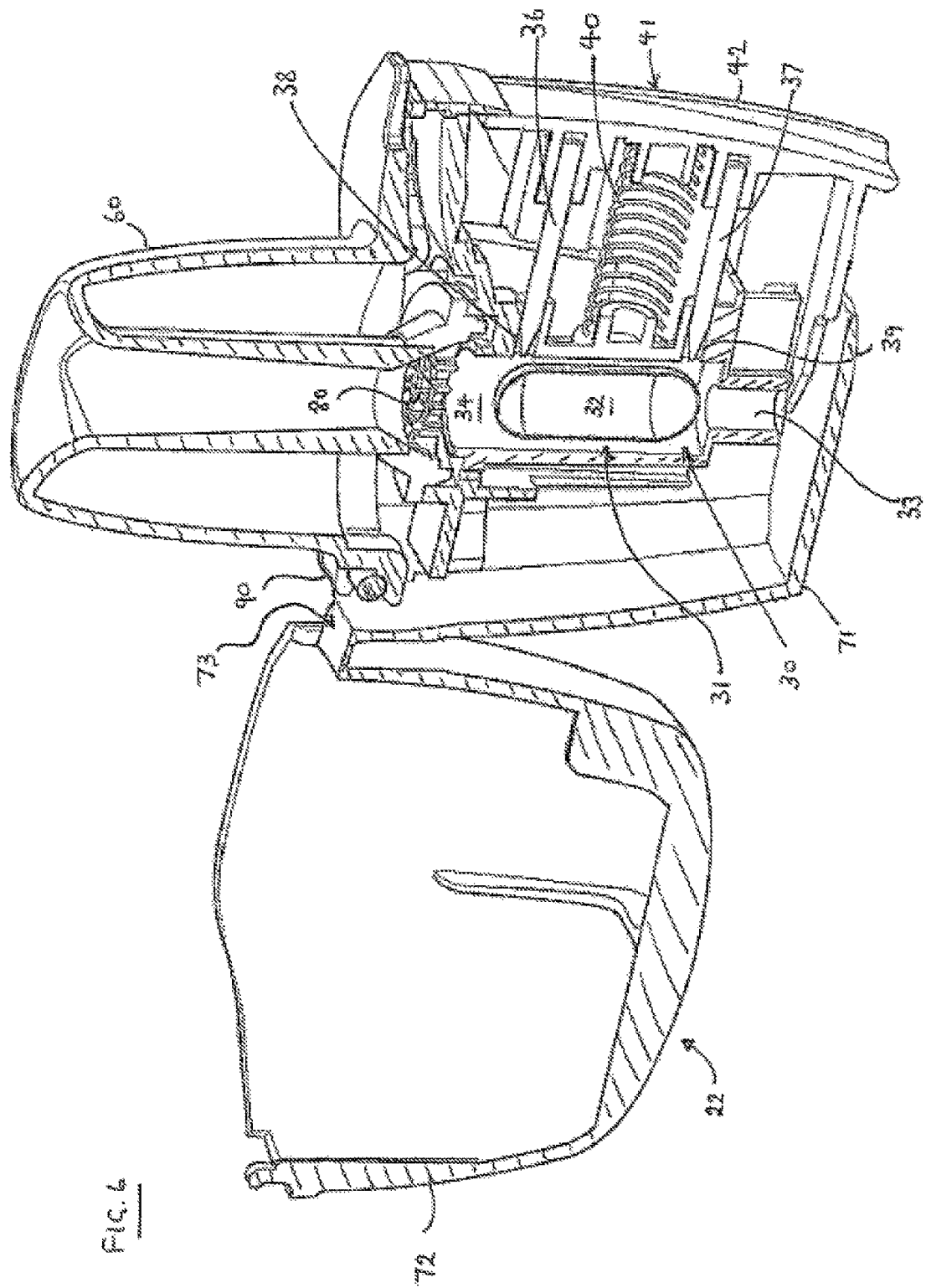
FIG. 6 shows a perspective view of the inhalator with a vertical cut-away in the vertical plane containing the long axis of the inhalator.

The chamber moulding 120 defines a capsule holder 30, including a capsule chamber 31 for receiving a capsule 32 containing the powdered preparation, the capsule chamber 31 having an air inlet opening 33 and an air outlet opening 34 (see FIG. 6).

Figure 7:
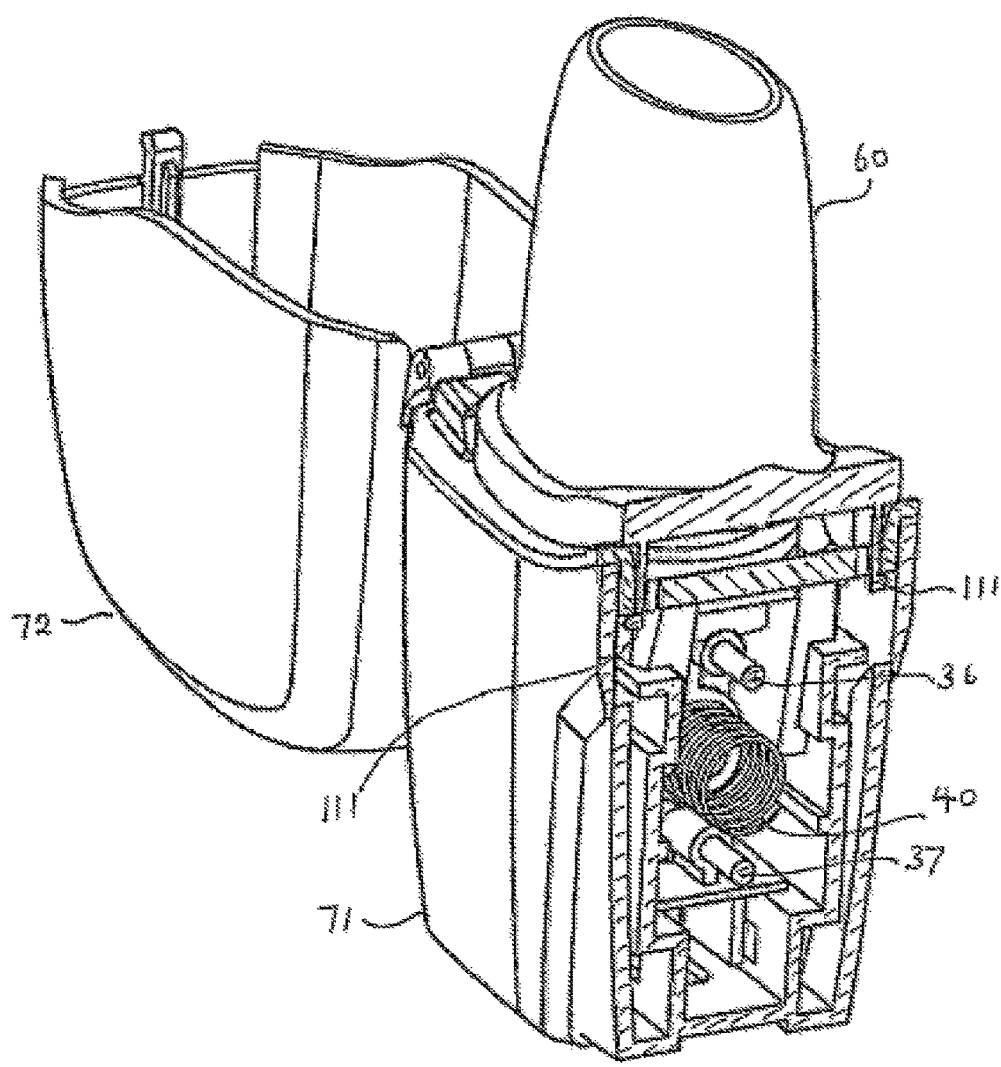
FIG. 7 shows a perspective view of the inhalator with a vertical cut-away in the vertical plane P shown in FIG. 2.
Figure 9:
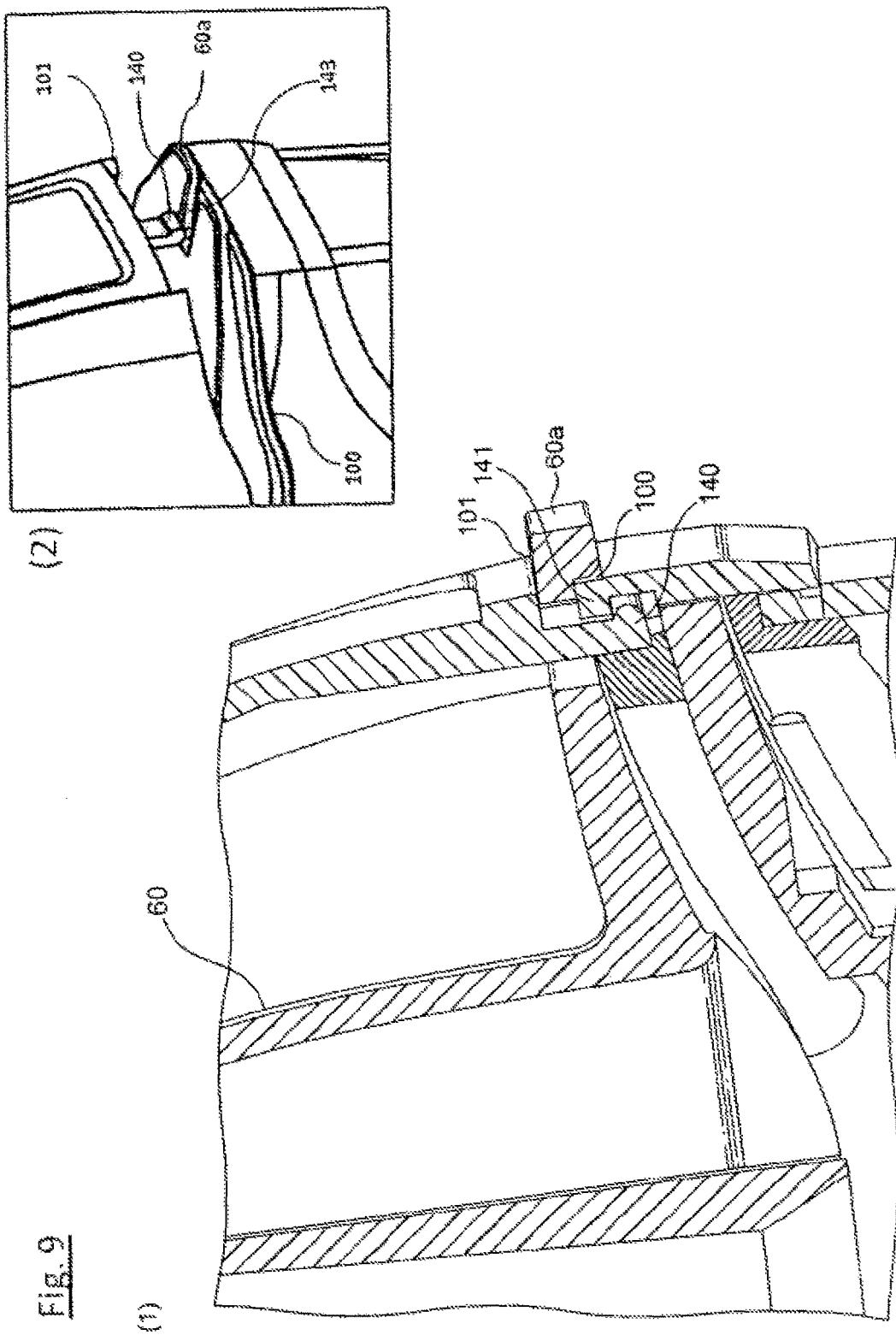
FIG. 9(1) and 9(2) shows detail (1=cross-section; 2=perspective) of the snap closure between the upper and lower parts of the outer shell.

Still with reference primarily to FIG. 6, and also to FIGS. 7 and 10, the inner part 20 of the inhalator has a capsule opening device 35 associated with the capsule chamber 31 for opening the capsule 32 within the chamber. The capsule opening device 35 in the illustrated example includes a pair of sharp pins 36, 37 mounted to one side of the chamber 31 and moveable into and out of the chamber 31 through respective guide channels 38, 39 against the restoring force of a spring 40. However, any suitable capsule opening device may be used. For example, one or more blade or drill may be used in place of or as well as pins. Although the illustrated capsule opening device uses two pins 36, 37, one pin or more than two may alternatively be used.

The pins 36, 37 of the capsule opening device pierce the wall of the capsule 32, which is typically constructed of a conventional pharmaceutical capsule material such as gelatine or a physiologically compatible plastic, and cause the powder formulation within the capsule to be drawn out of the capsule into an airflow generated by the user, by virtue of the Bernoulli effect as described in the prior art acknowledged above.

The capsule opening device is mounted to the actuator moulding 130, which defines a finger-operable actuator 41 for the capsule opening device. In the illustrated example the actuator 41 includes an external finger-operable button 42 mounted on the capsule holder 30 and capsule opening device 35 to provide an assembly A of the chamber and actuator mouldings 120, 130, including particularly the capsule holder 30, capsule opening device 35 and actuator 41. The actuator is arranged to actuate the capsule opening device 35 by finger pressure applied to the button 42. The button slides along guide rails 43, 44 (corresponding parts (not shown) are behind as viewed on FIG. 10) arranged in two pairs on opposite sides of the assembly and pushes the pins 36, 37 into the chamber 31 as described above. A pair of stops 47, 48 is provided, one stop on each side of the assembly, to limit the forward extent of movement of the finger button 42 (see particularly FIG. 10).

Any suitable actuator for the capsule opening device may be used. For example, the capsule opening device may be fixed with respect to the remainder of the inhalator, and the capsule holder 30 may be arranged to move with respect to the capsule opening device. In that alternative arrangement the actuator may suitably be arranged to actuate the capsule opening device by finger pressure applied to the button. The button may slide along guide rails and the capsule holder may be mounted on a carriage carried by the rails, so that finger pressure applied to the button will push the capsule holder onto the pins (which may pass through guide channels provided through the wall of the chamber).

Multiple actuators for the capsule opening device may be used, and in this case they may act on the capsule from the same or different directions. For example, a pair of opposed actuators may be manually squeezed to cause one or more suitably arranged capsule opening devices to open the capsule in the chamber.

The capsule opening device may act on the capsule in a single action, as in the illustrated example, or in multiple actions. Multiple actions may be simultaneous, sequential or a combination of both.

Figure 1:
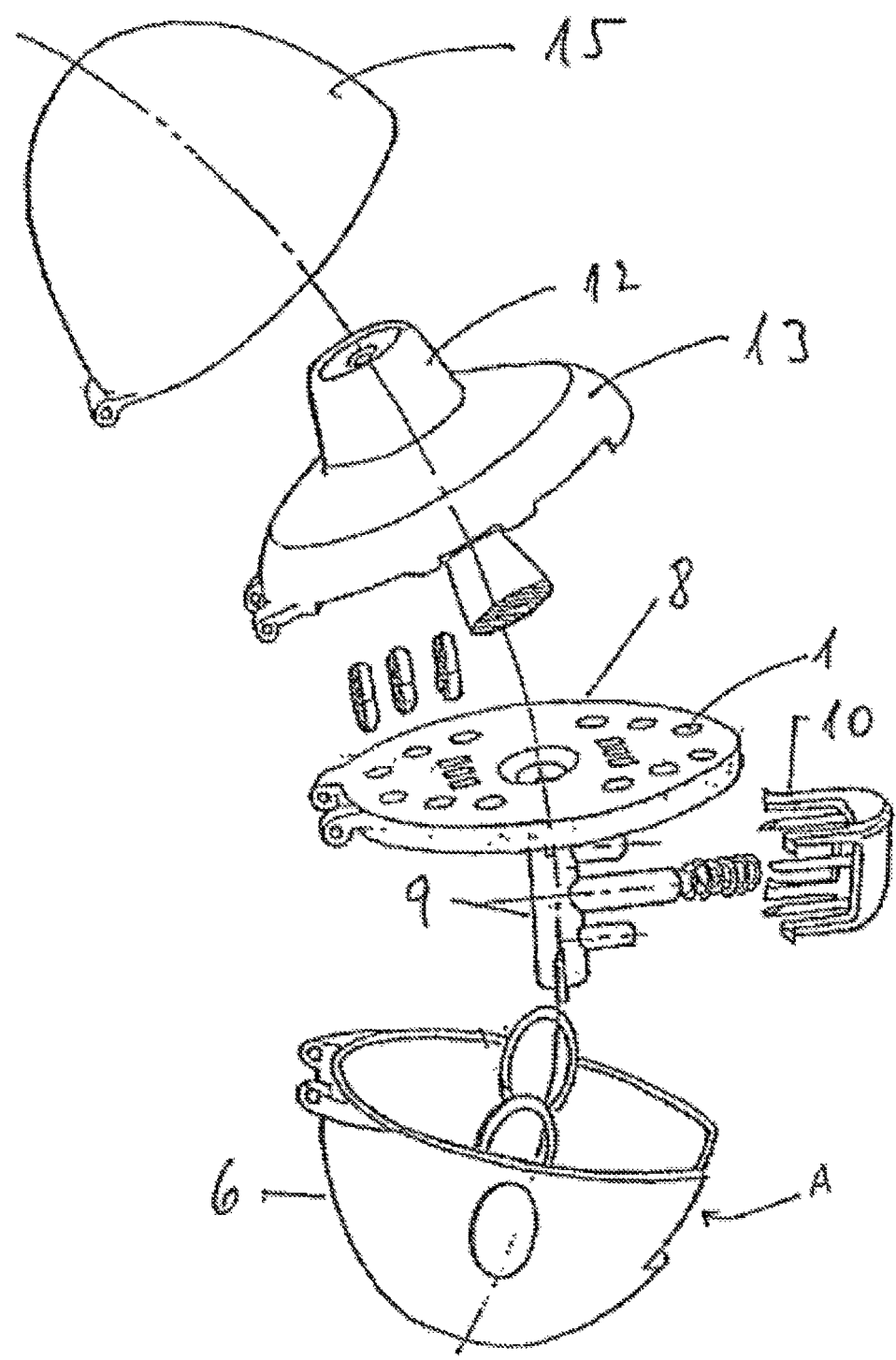
FIG. 1 reproduces FIG. 6 of WO-A-94/28958 (known inhalator)
Figure 2:
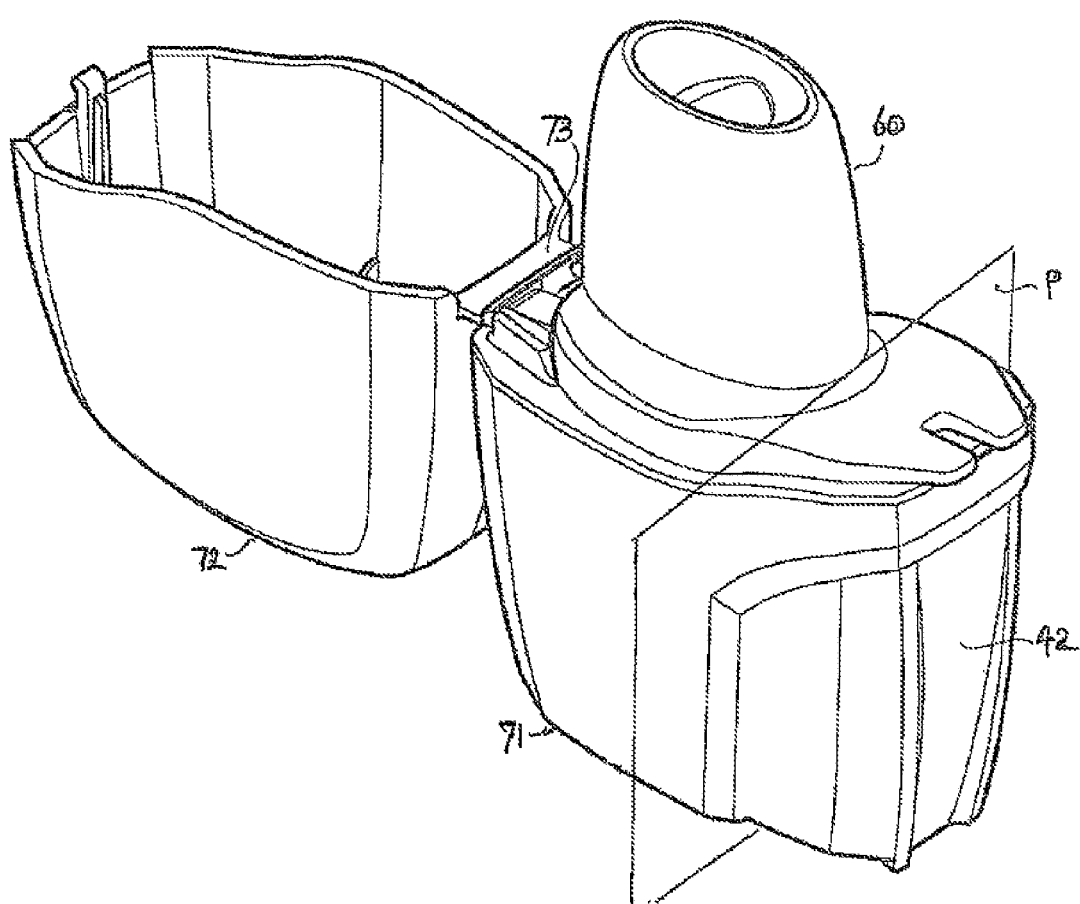
FIG. 2 shows a top perspective view from front and side of an inhalator embodying the present disclosure with the upper part of the outer shell open, showing the mouthpiece.
Figure 3:
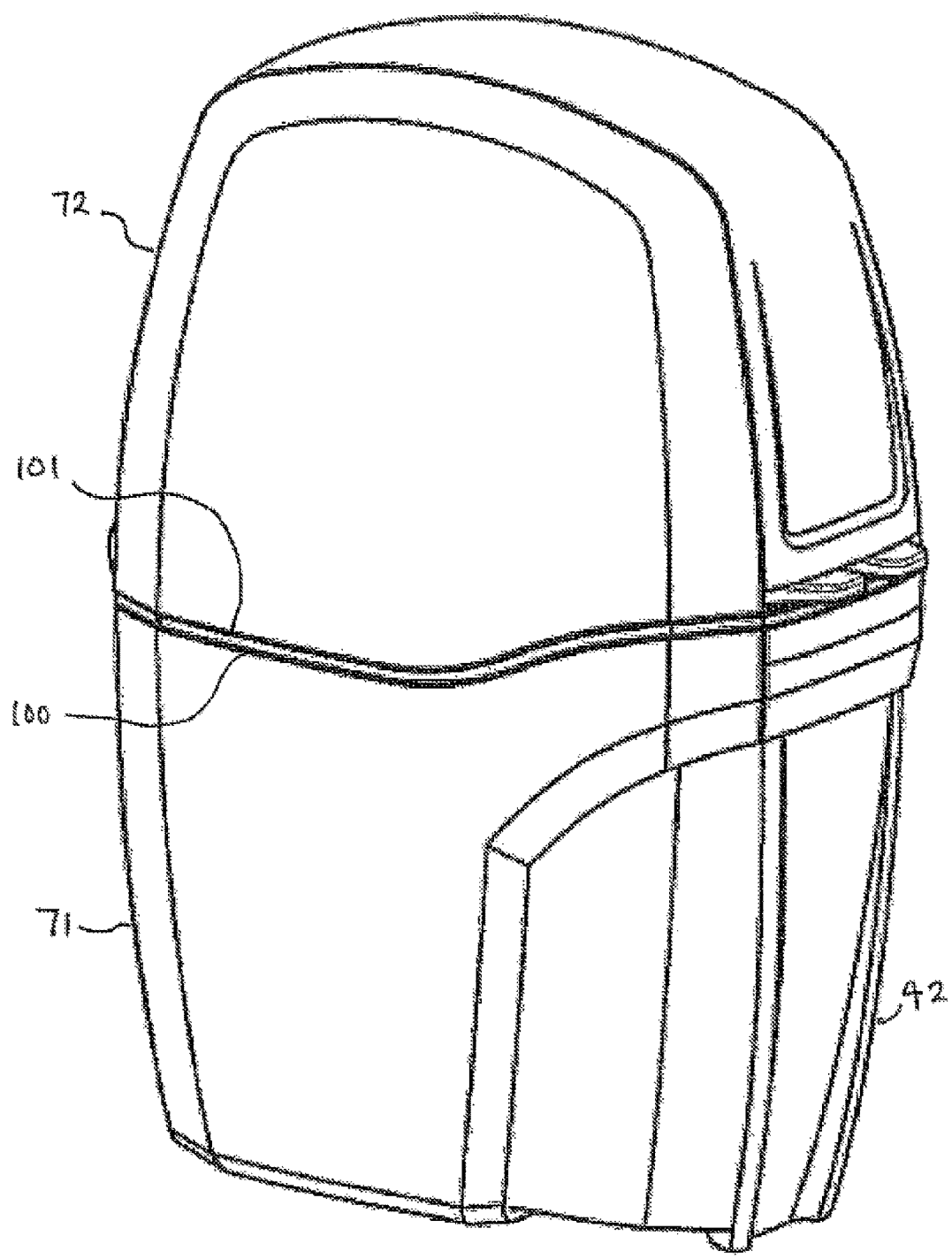
FIG. 3(1), 3(2), 3(3), 3(4), 3(5) and 3(6) shows the process of opening the inhalator from the closed condition (1) to the loading condition with the upper part of the outer shell in the open condition retaining the mouthpiece for loading the chamber (3) to the condition for use (4) to the emptying condition (6) for emptying the chamber.
Figure 3:
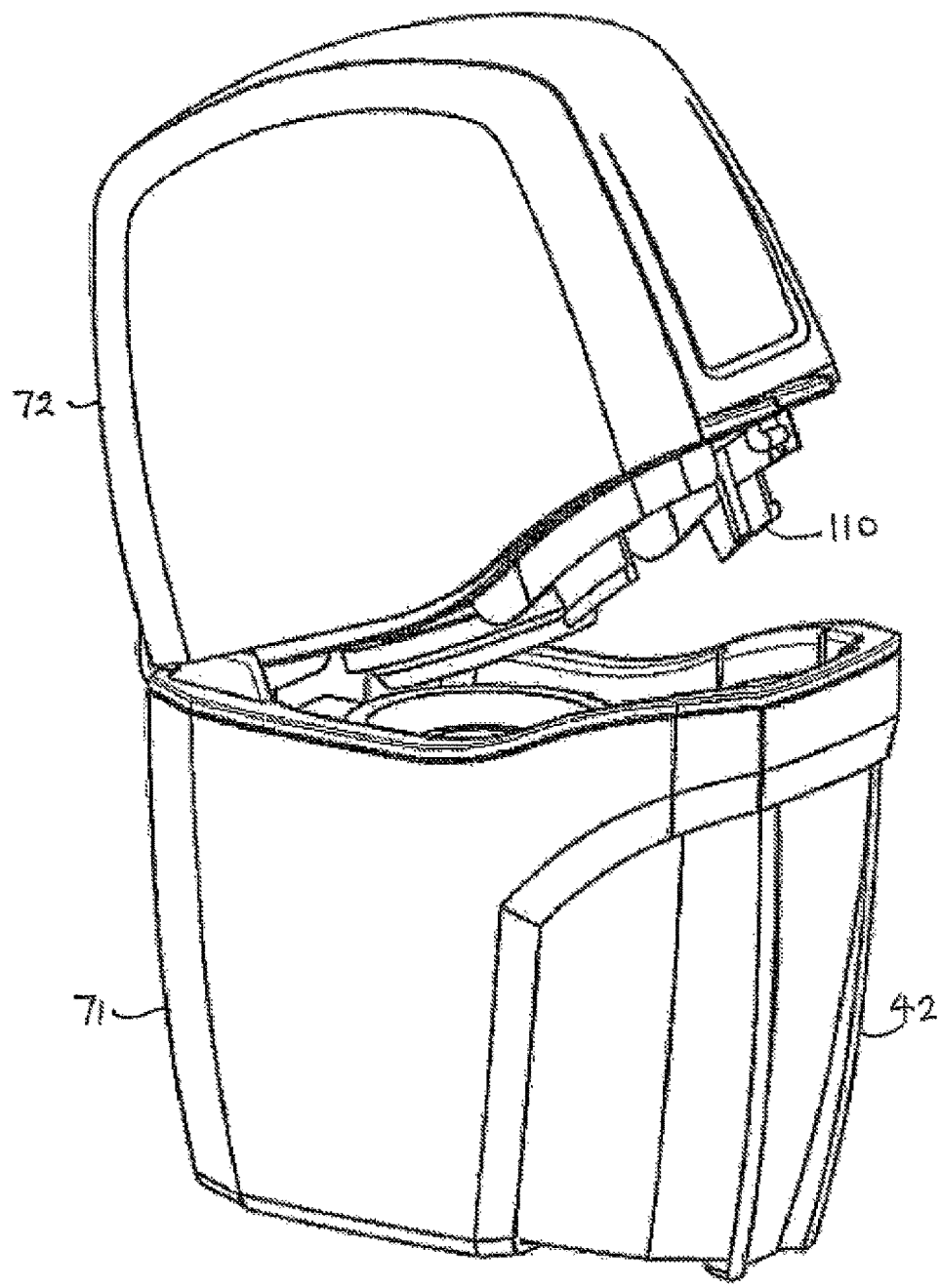
Figure 3:
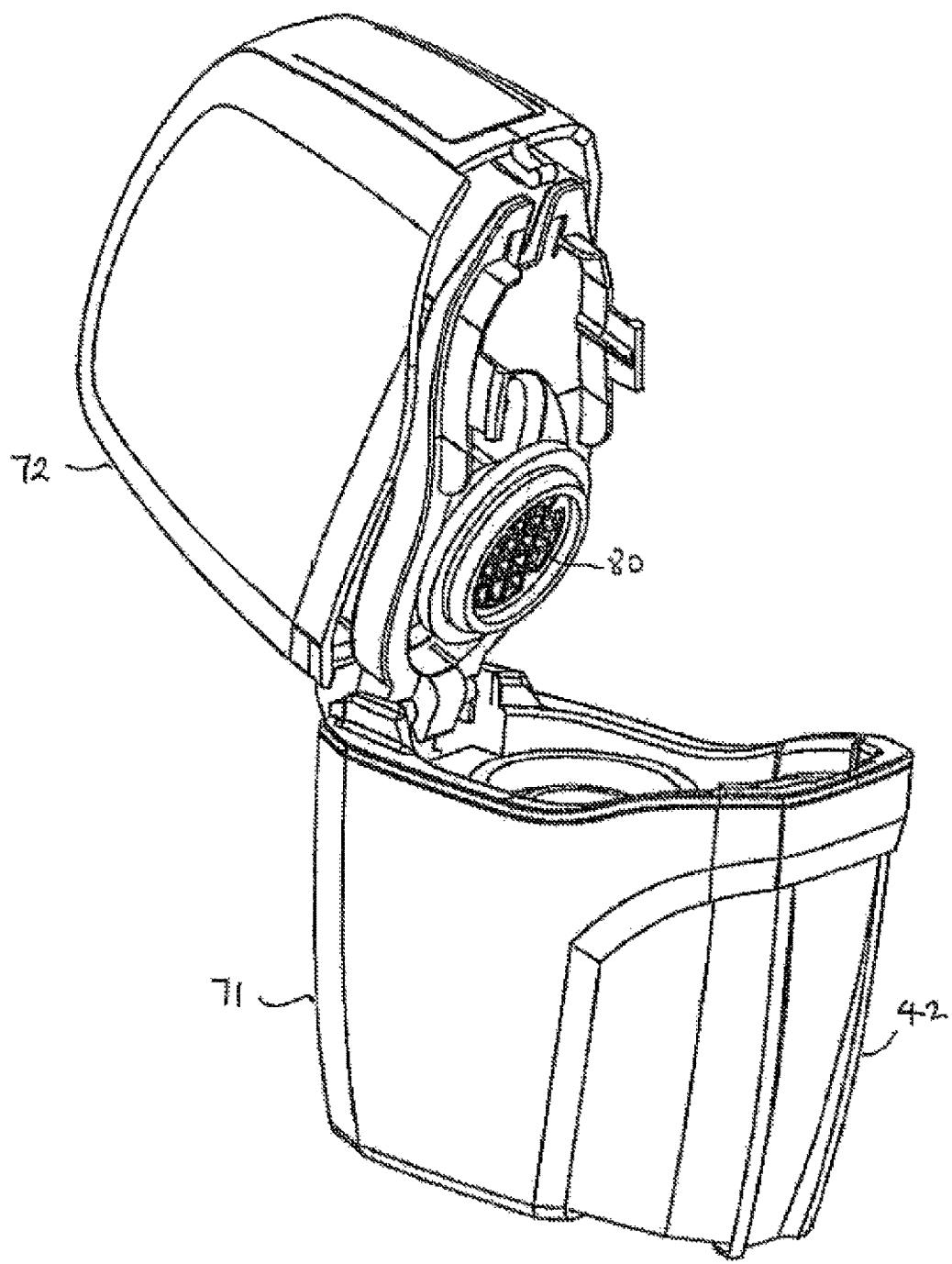

Hinged to the assembly of the capsule holder 30, capsule opening device 35 and actuator 41 is a mouthpiece 60. Referring particularly to FIGS. 2 and 3, the mouthpiece 60 can pivot between an open condition in which the mouthpiece is spaced apart from the air outlet opening 34 of the capsule chamber 31 for loading the capsule into the capsule chamber (see FIG. 3(3)) and a closed condition in which the mouthpiece is disposed in airflow communication with the air outlet opening 34 of the capsule chamber 31 for use (see FIG. 3(4) and FIG. 2).

In the said closed condition (FIG. 3(4) and FIG. 2), the user can suck air through the air inlet opening 33, into the capsule chamber 31 to entrain powder from the opened capsule 32, and then out of the chamber through the air outlet opening 34 and the mouthpiece 60, and thence into the user's lungs.

Referring particularly to FIGS. 2 to 4 and 6, the inhaler further includes the outer part 22 mentioned generally above. The outer part 22 is a rigid outer shell including a lower shell part 71 hinged to an upper shell part 72 via a web 73 of flexible material so that the shell is openable and closable. The outer part 22 as illustrated is constructed as a one-piece moulding, suitably in a mouldable plastic, whereby the lower shell part 71, the upper shell part 72 and the web 73 forming the hinge are formed simultaneously together from the same material. Alternatively, portions of the outer part 22 may be formed separately and subsequently assembled and bonded together in conventional manner.

Figure 5:
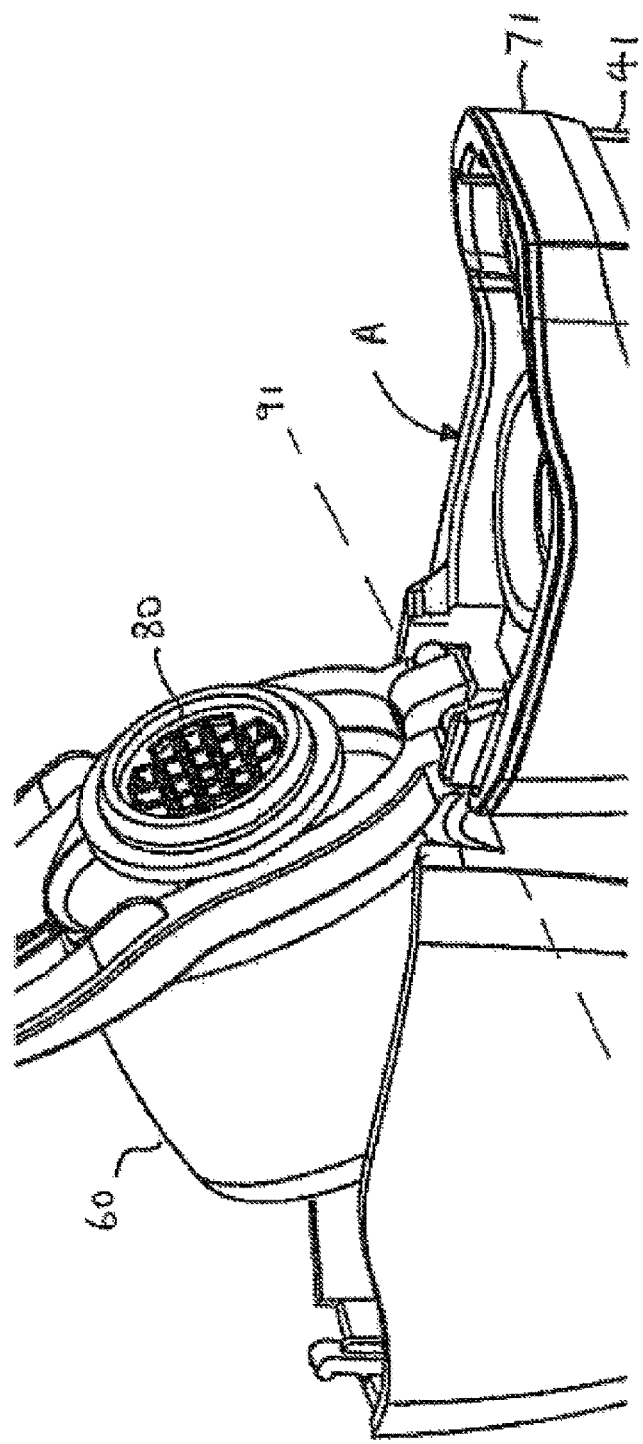
FIG. 5 shows detail of the hinge system between the assembly and the mouthpiece.

A grille 80 is provided on the underside of the mouthpiece 60, as shown particularly in FIGS. 4 to 6. The grille 80 serves to prevent any possible broken pieces of the wall material of the capsule 32 from being sucked into the user's lungs.

Referring particularly to FIGS. 4 to 8, the arrangement by which the mouthpiece 60 is hinged to the assembly of the capsule holder 30, capsule opening device 35 and actuator 41 will now be described.

The mouthpiece 60 is hinged to the assembly of the capsule holder 30, capsule opening device 35 and actuator 41, this assembly being generally denoted A in FIGS. 4 and 5. It is preferred that the hinge system includes projections and recessed on the respective parts that engage with each other to provide a hinge, with no additional parts such as pins being required. It is preferred that the hinge between assembly A and mouthpiece 60 is a separable hinge, so that if too much pressure is exerted on the mouthpiece 60 when pivoting it away from the assembly A, for example when opening the chamber 31 for loading or emptying the chamber 31, or when seeking to remove the assembly A and mouthpiece 60 from the shell as described in the following paragraph, the hinge will separate before breaking. The construction is preferably a simple snap-fit or push-fit engagement system of cooperating formations on the two parts of the hinge, so that the user in the case of separation of the parts can easily reassemble the hinge.

As shown in more detail in FIGS. 4, 5, 6 and 8, the mouthpiece 60 includes a pair of projections 90 extending away from the pivot line 91 of the hinge (shown as a dotted line) on the opposite side of the pivot line 91 from the mouthpiece 60, and the assembly A includes a corresponding pair of stop surfaces (not shown) arranged so that the said projections 90 will bear against the stop surfaces after the mouthpiece 60 has been rotated more than a certain angle (e.g. more than about 90°, more than about 100°, more than about 110° or more than about 120°) out of the closed condition in which the mouthpiece 60 is adjacent the air outlet opening 34 of the capsule chamber 31 (this closed condition is illustrated in FIG. 6). FIG. 4(1) shows the situation at the point that this critical angle (as illustrated: 110°) is reached. The arrow B shows the 110° extent of opening that the mouthpiece 60 has travelled through. FIGS. 4(2) and (3) show the situation if, after the certain angle of rotation has been reached, further gentle pressure is applied to rotate the mouthpiece 60 further in the direction of arrow B, i.e. beyond 110°. The interaction between the projections 90 and the stop surfaces causes the hinge to lock, and further pressure on the mouthpiece will lift the assembly A out of its fit in the lower shell part 71, which assists to remove the assembly from the shell in the direction of arrows C in FIGS. 4(3) and (4).

The mouthpiece 60 and the assembly A are provided with cooperating surfaces that engage with each other to lock the mouthpiece 60 to the assembly A in the closed condition, when the mouthpiece 60 is rotated to lie adjacent the air outlet opening 34 of the capsule chamber 31 (as shown in FIG. 6). It is preferred that the cooperating surfaces secure the mouthpiece 60 to the assembly A in a snap-fitting manner. FIGS. 8(1) and (2) illustrates the surfaces in more detail. Downward arms 110 extending from the mouthpiece 60 (also visible in FIGS. 3 and 4, for example) carry mutually outwardly directed flanges 111 which engage in a snap-fit manner with the surfaces defined by slots (not shown) in the upper part of the chamber moulding 120. The engagement between the mouthpiece 60 and the assembly A is weak enough that the mouthpiece can be manually hinged away from the assembly, as described in more detail below.

The parts of the rigid outer shell of the inhaler are hollow and each has a circumferential rim defining an open mouth of the part. The rim of the lower shell part 71 is denoted 100 in FIGS. 3 and 4. The rim of the upper shell part 72 is denoted 101 in FIGS. 3 and 4. The outer shell of the inhaler is arranged so that the rim contour of one shell part matches the rim contour of the other completely circumferentially around the rims when the shell is in the closed condition (see FIG. 3(1)). The rims are configured to lie parallel to each other around their whole circumference in the closed condition of the shell. This matching of the rim contours takes place even though the rims may not be in contact—for example, in the illustrated arrangement, a portion 60*a* of the mouthpiece 60 is interposed between the rims 100, 101 in the closed condition (see FIG. 9)

The lower shell part 71 of the outer shell is tapered inwardly in the downward direction away from a top opening defined by its rim 100, and the assembly A of the chamber 120 and actuator 130 mouldings correspondingly tapers inwardly in the downward direction so that it can be received in the lower shell part 71, the finger-operable actuator 42 for the capsule opening device protruding through an opening in the lower shell part 71 below the rim 100, as shown for example in FIG. 4(1), whereby the rim 100 of the lower shell part is complete and the hinged unit of the assembly A and the mouthpiece 60 can be removed from the lower shell part 71 by passing up and through the top opening defined by the rim 100 of the lower shell part 71, as shown in FIGS. 4(3) and (4).

This arrangement has the technical advantage that the two shell parts 71 and 72 are more rigid and robust that the arrangement of the known inhalators, in which the rim of the lower shell part was cut away.

The two parts 71, 72 of the shell fit securely, but manually releasably, to each other in the closed condition of the shell (FIG. 3(1)). This is illustrated in more detail in FIG. 9. Cooperating formations 140, 141 provided on the rims 100, 101, are provided on matching parts of the two parts of the shell, associated with the rims of the shell parts, to provide for push-fit or snap-fit engagement that is secure, but releasable with finger pressure by a normal user. The formation 140 provided on the upper shell part 72 passes through an aperture 143 in the part 60*a* of the mouthpiece 60 that lies between the two matching rims 100, 101 of the shell parts.

The assembly A of the capsule holder 30, capsule opening device 35 and actuator 41, together with the mouthpiece 60, define a first hinged unit 20.

The outer shell 71, 72 defines a second hinged unit 22.

The first hinged unit 20 is disposed within the second hinged unit 22 for use such that the first hinged unit 20 can be removed as such from the second hinged unit 22 as such. The arrangement is particularly characterized in that the hinges of the two units 20, 22 are separate from one another. In particular, the hinge of the first unit 20 is separate and operates independently of the hinge of the second unit 22. The first unit can be removed from the second unit without affecting the construction or operation of either hinge (see FIG. 4).

The inhalator may include treatment regimen recorders, prompters, calculators or other assisting devices, for example electronic devices. Such devices may, for example, be associated with the rigid outer shell 71, 72.

The parts of the present inhalator may be conveniently manufactured in plastics materials, e.g. by injection moulding or other suitable moulding.

The operation of the inhalator is illustrated generally in the parts of FIG. 3. Starting from the completely closed condition illustrated in FIG. 3(1) (first and second hinged units both closed, first inside the second), the user manually opens the upper part 72 of the outer shell (FIG. 3(2)), disconnecting the cooperating formations 140, 141 that secure the upper shell part to the lower shell part in the closed condition of the outer shell. Simultaneously, the user disconnects the cooperating formations 110 from the slots in the upper part of the chamber moulding 120, so that the mouthpiece 60 pivots away from the chamber moulding 120 and reveals the capsule chamber 31 (FIG. 3(3)). The user then inserts a capsule 32 into the chamber 31 and snap closes the mouthpiece 60 onto the chamber moulding 120 (FIG. 3(4)). The inhalator is then ready for use. The user depresses the actuator button 42 for the capsule opening device, so opening the capsule in the chamber 31. The user then sucks air through the chamber, entraining the powder from the capsule, and thence draws the air and the powder into his lungs.

After completion of the powder inhalation, the user again disconnects the cooperating formations 110 from the slots in the upper part of the chamber moulding 120, so that the mouthpiece 60 pivots away from the chamber moulding 120 and reveals the capsule chamber 31 (FIG. 3(5)). The capsule debris can then be emptied out of the chamber 31. After cleaning of the chamber, the user closes the upper shell part 72 back onto the lower shell part 71 so that the cooperating formations 140, 141 of the shell parts are snap engaged (FIG. 3(5) shows the upper shell part half closed). This closure returns the inhalator to the resting (fully closed) condition of FIG. 3(1), ready for the next use.

Figure 11:
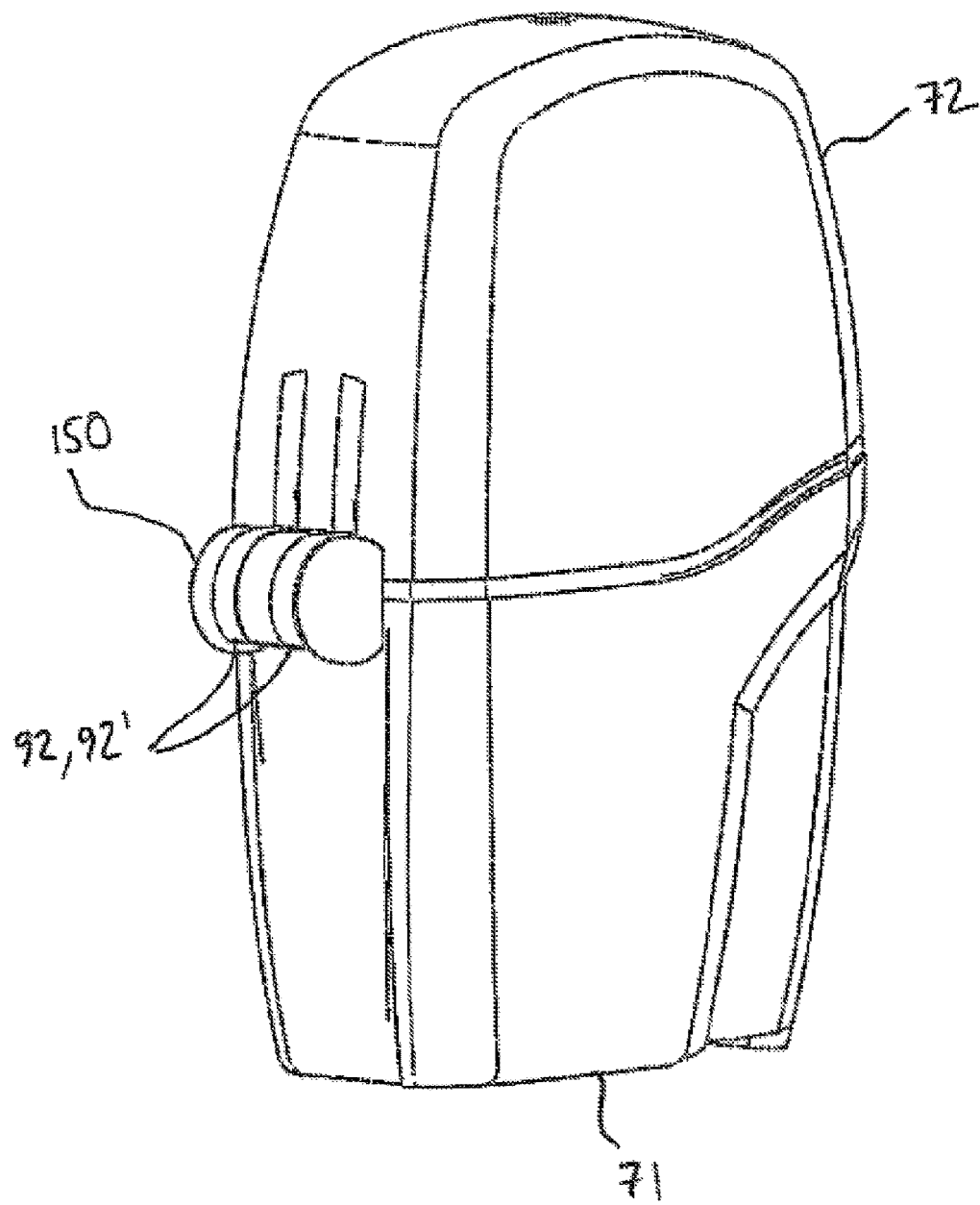
FIG. 11 shows a perspective view of an alternative inhalator embodying the present disclosure in a closed condition.
Figure 12:
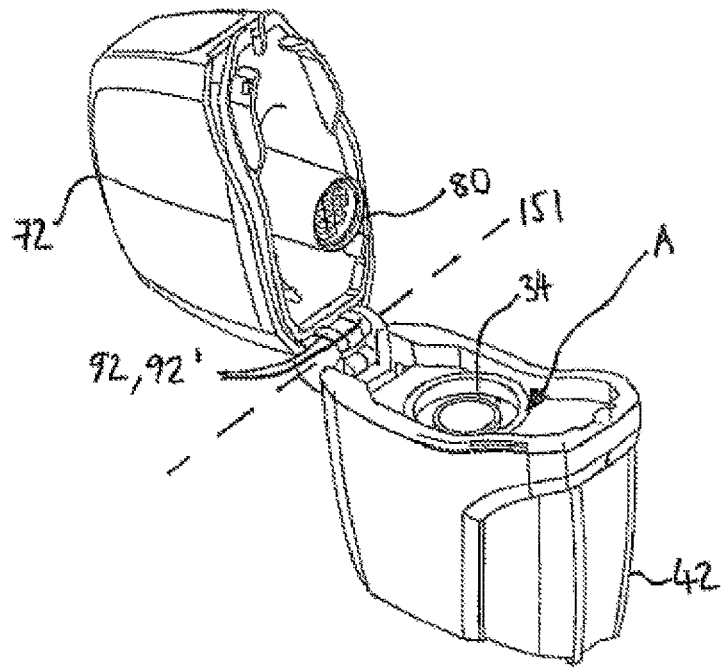
FIG. 12(1) shows a perspective view of the inhalator of FIG. 11 with the upper part of the outer shell in the open condition with the mouthpiece in the upper part of the outer shell for loading the chamber, and FIG. 12(2) shows the same perspective view with the mouthpiece not in the upper part of the outer shell.
Figure 12:
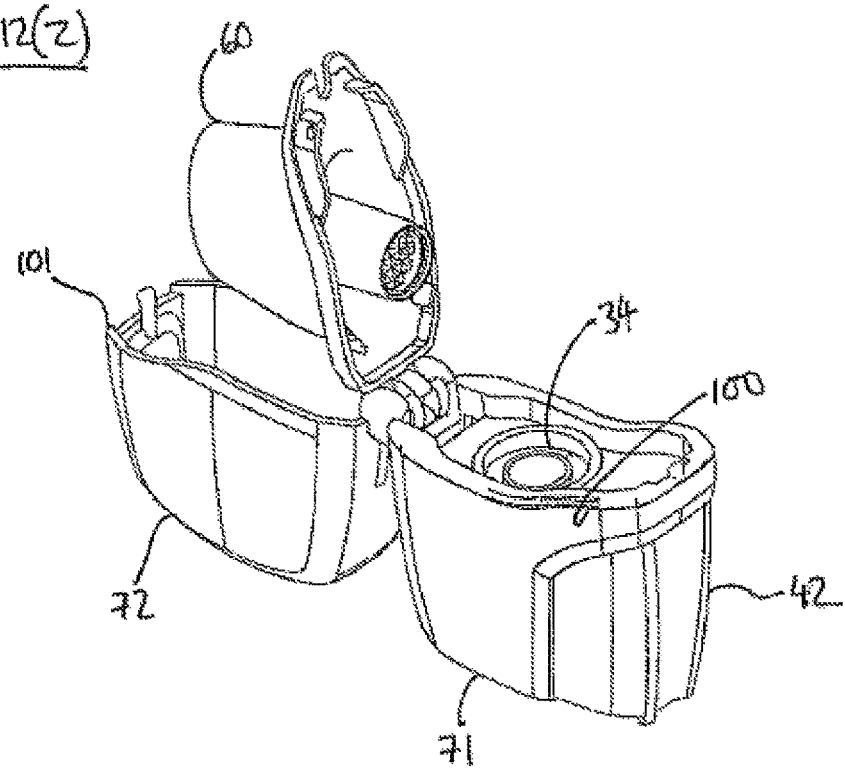
Figure 13:
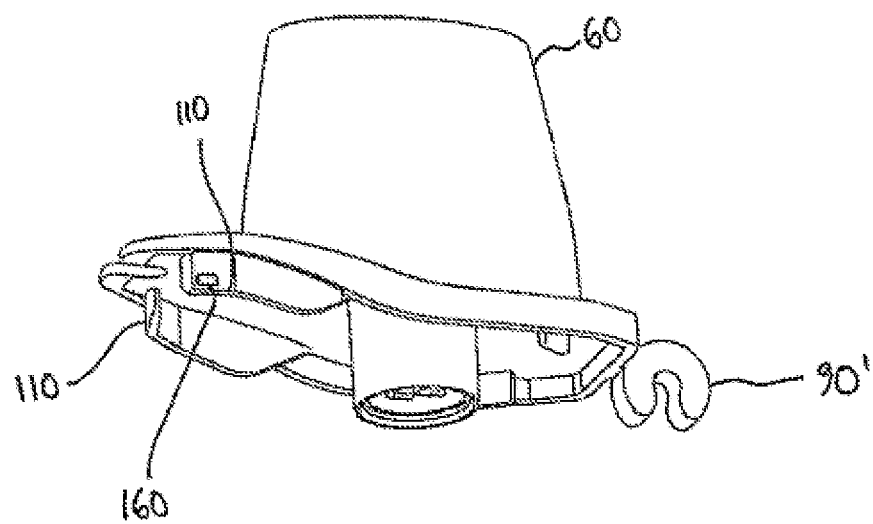
FIG. 13(1) shows a perspective view from below and the side of the mouthpiece of the inhalator of FIG. 11, and FIG. 13(2) shows a perspective view from above and the side of the lower part of the outer shell containing the assembly (a) as present in the inhalator of FIG. 11.
Figure 13:
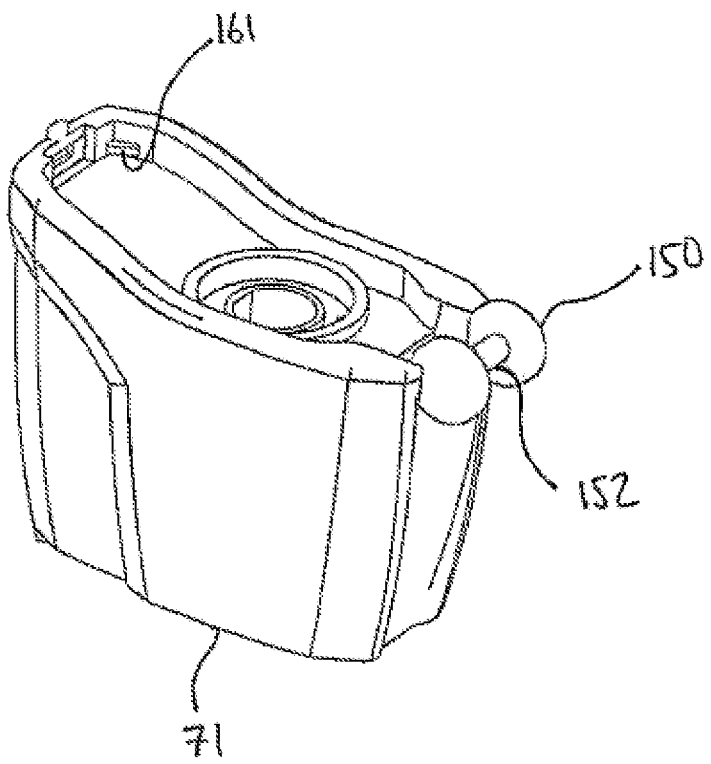

Referring to FIGS. 11 to 13, there is shown an alternative inhalator for the inhalation of powdered drug preparations from capsules which contain the powdered preparations. Parts in common with the inhalator described above are provided with the same reference numerals, while new parts are provided with new reference numerals.

The form, and mode of operation, of this particular example corresponds broadly to that described above, with the differences discussed below.

FIGS. 11 to 13 show generally an inhalator including a lower outer shell part 71 and an upper outer shell part 72. The lower outer shell part 71 is provided with a hinge pin 152 having terminal enlarged stops 150 (shown in more detail in FIG. 13(2)) to retain pivotable parts that are sleeved around the hinge pin 152, as described below.

FIGS. 12(1) and (2) show the inhalator in an open condition. Assembly A, including the capsule holder, capsule opening device and actuator (analogously to the description of the corresponding parts of the inhalator shown in FIGS. 2 to 10), is snap-fitted within the lower outer shell part 71 and is not directly hinged to the mouthpiece 60. Instead, the mouthpiece 60 is provided with a C-shaped formation 90' (shown in more detail in FIG. 13(1)) which clips onto the hinge pin 152 and is rotatably sleeved around the hinge pin to provide for pivoting movement of the mouthpiece relative to the lower outer shell part 71. The upper shell part is provided with two C-shaped formations 92, 92', which also clip onto the hinge pin 152, on either side of the formation 90' of the mouthpiece, and are also rotatably sleeved around the hinge pin to provide for pivoting movement of the upper shell part 72 relative to the lower outer shell part 71. The common pivot line for all these directly hinged parts, namely the axis of the hinge pin 152, is shown as dotted line 151 in FIG. 12(1).

In this way, mouthpiece 60 can pivot between an open condition in which it is spaced apart from air outlet opening 34 of assembly A for loading a capsule into the capsule chamber, and a closed condition in which mouthpiece 60 is disposed in airflow communication with air outlet opening 34 (not shown).

Assembly A is retained in the lower outer shell part 71, preferably by means of a snap-fit or push-fit connection. Projections 161 provided inside the rim of the lower shell part 71 prevent accidental removal of assembly A.

As shown particularly in FIGS. 13(1) and (2), the mouthpiece 60 is provided with downwardly extending flanges 110, provided with outwardly extending projections 160. Projections 160 cooperate with the internal wall of the rim of the lower shell part 71 to provide a friction fit when the mouthpiece is in the closed condition, releasable with finger pressure in normal use.

The foregoing broadly describes the present disclosure without limitation to particular implementations. Variations and modifications as will be within the abilities of those skilled in this art are intended to be included in the scope of this disclosure as defined in and by the appended claims.

The invention claimed is:

1. An inhalator for the inhalation of powdered drug preparations from capsules which contain the powdered preparations, the inhalator comprising:

a rigid outer shell comprising a lower shell part hinged to an upper shell part so that the rigid outer shell is openable and closable;
an assembly non-hingedly disposed within the lower shell part, the assembly comprising:
   a capsule holder comprising a capsule chamber for receiving a capsule containing the powdered preparation, the capsule chamber having an air inlet opening and an air outlet opening;
   a capsule opening device for opening a capsule within the capsule chamber; and
   a finger-operable actuator for the capsule opening device; and
a mouthpiece or nosepiece;
   the mouthpiece or nosepiece being configured for a user to suck air through the air inlet opening, into the capsule chamber to entrain powder from the opened capsule, and then out of the chamber through the air outlet opening and the mouthpiece or nosepiece, and thence into the user's lungs;
   the-mouthpiece or nosepiece being disposed relative to the assembly to pivot between an open condition in which the mouthpiece or nosepiece is spaced apart from the air outlet opening of the capsule chamber for loading the capsule into the capsule chamber and a closed condition in which the mouthpiece or nosepiece is disposed in airflow communication with the air outlet opening of the capsule chamber for use;
the inhalator further comprising, defining or being disposed as follows:
   the assembly and the mouthpiece or nosepiece defining a first hinged unit, the mouthpiece or nosepiece being hingedly disposed by a separable hinge to move relative to the assembly, so that the separable hinge will separate before breaking and the outer shell defining a second hinged unit, the first hinged unit being disposed within the second hinged unit for use, the mouthpiece or nosepiece being hingedly connected to the outer shell and being hingedly moveable relative thereto;
   the finger-operable actuator being arranged flush in the lower shell part, not projecting outside the inhalator irrespective of the position of the upper shell part relative to the first hinged unit;
   the assembly and the mouthpiece or nosepiece being disposed within the outer shell, each of the upper and lower shell parts having a circumferential rim defining a mouth and the contours of the rim of each shell part match the contours of the rim of the other shell part completely around the rims when the outer shell is in the closed condition;
   the assembly and the lower shell part being adapted so that the assembly is snug-fit or push-fit or snap-fit into the lower shell part for locating the assembly in the lower shell part, with projections provided on and inside the rim of the lower shell part to prevent accidental removal of the assembly therefrom; and
   the upper part of the outer shell being configured to fit manually releasably to the mouthpiece or nosepiece in the closed condition of the outer shell, so that opening of the outer shell by a user in preparation for use correspondingly pivots the mouthpiece or nosepiece away from the assembly to expose the capsule chamber for loading of a capsule.

2. An inhalator according to claim 1, the assembly being received completely within the lower shell part of the outer shell.

3. An inhalator according to claim 1, the inhalator having a single capsule chamber.

4. An inhalator according to claim 1, the lower shell part of the outer shell being tapered inwardly in a direction away from a top opening defined by its rim, the assembly correspondingly tapering inwardly so that it is received in the lower shell part, and the finger-operable actuator for the capsule opening device protrudes through an opening in the lower shell part below the rim of the lower shell part, the rim of the lower shell part being complete and the assembly being configured to be removed from the lower shell part by passing up and through the top opening defined by the rim of the lower shell part.

5. An inhalator according to claim 4, the assembly being configured to be removed from the lower shell part by passing up and through the top opening defined by the rim of the lower shell part.

6. An inhalator according to claim 1, the mouthpiece or nosepiece being adapted to fit manually releasably to the assembly in a closed condition in which the mouthpiece or nosepiece is disposed adjacent the air outlet opening of the capsule chamber.

7. An inhalator according to claim 1, the lower shell part and the upper shell part being adapted to fit manually releasably to each other in the closed condition of the shell.

8. An inhalator according to claim 1, the mutual hinging of the assembly and the mouthpiece or nosepiece being provided by direct hinged connection between the parts.

9. An inhalator according to claim 1, configured for use with a capsule formed of a material selected from gelatine, hydroxypropylmethyl cellulose, hydroxypropyl cellulose, or any combination thereof.

10. A method for using an inhalator for use in inhaling powdered medicaments; the inhalator comprising
   an assembly comprising a capsule chamber for receiving a capsule containing the powdered preparation, the capsule chamber having an air inlet opening and an air outlet opening; a capsule opening device for opening a capsule within the capsule chamber; and a finger-operable actuator for the capsule opening device;
   a mouthpiece or nosepiece; and
   a rigid outer shell comprising a lower shell part hinged to an upper shell part so that the shell is openable and closable;
   the assembly being non-hingedly disposed within the lower shell part; and the finger-operable actuator being arranged flush in the lower shell part, not projecting outside the inhalator irrespective of the position of the upper shell part relative to the assembly;
   the mouthpiece or nosepiece hingedly connected to the lower shell part and disposed to move relative to the assembly, by a separable hinge so that the separable hinge will separate before breaking, to pivot between an open condition in which the mouthpiece or nosepiece is spaced apart from the air outlet opening of the capsule chamber for loading the capsule into the capsule chamber and a closed condition in which the mouthpiece or nosepiece is disposed in airflow communication with the air outlet opening of the capsule chamber for use,
   the assembly and the lower shell part being adapted so that the assembly is snug-fit or push-fit or snap-fit into the lower shell part for locating the assembly in the lower shell part, with projections provided on and inside the rim of the lower shell part to prevent accidental removal of the assembly therefrom, and the upper part of the outer shell being configured to fit manually releasably to the mouthpiece or nosepiece in the closed condition of the outer shell, so that opening of the outer shell by a user in preparation for use correspondingly pivots the mouthpiece or nosepiece away from the assembly to expose the capsule chamber for loading of a capsule;

the method including inserting in the capsule chamber of the inhalator a capsule which contains a powdered preparation; and, having the user suck air through the air inlet opening, into the capsule chamber to entrain powder from the opened capsule, and then out of the chamber through the air outlet opening and the mouthpiece or nosepiece.

* * * * *